US010300190B2

United States Patent
Stuva et al.

(10) Patent No.: US 10,300,190 B2
(45) Date of Patent: May 28, 2019

(54) TARGET VOLUME BASED DIAPHRAGM REPOSITIONING FOR PRESSURE MEASUREMENT APPARATUS

(71) Applicant: GAMBRO LUNDIA AB, Lund (SE)

(72) Inventors: Rickie L. Stuva, New Hope, MN (US); John O'Mahony, Maple Grove, MN (US)

(73) Assignee: Gambro Lundia AB, Lund (SE)

( * ) Notice: Subject to any disclaimer, the term of this patent is extended or adjusted under 35 U.S.C. 154(b) by 655 days.

(21) Appl. No.: 14/650,920

(22) PCT Filed: Dec. 16, 2013

(86) PCT No.: PCT/US2013/075367
§ 371 (c)(1),
(2) Date: Jun. 10, 2015

(87) PCT Pub. No.: WO2014/099767
PCT Pub. Date: Jun. 26, 2014

(65) Prior Publication Data
US 2015/0306299 A1 Oct. 29, 2015

Related U.S. Application Data

(60) Provisional application No. 61/739,973, filed on Dec. 20, 2012.

(51) Int. Cl.
*A61M 1/36* (2006.01)
*A61M 1/16* (2006.01)
(Continued)

(52) U.S. Cl.
CPC ............ *A61M 1/3607* (2014.02); *A61M 1/16* (2013.01); *A61M 1/34* (2013.01); *A61M 1/3403* (2014.02);
(Continued)

(58) Field of Classification Search
CPC .............. A61M 1/3639; A61M 1/3607; A61M 1/3609; A61M 1/3403; A61M 1/34; A61M 1/16; A61M 2205/3331; A61M 2205/3358
See application file for complete search history.

(56) References Cited

U.S. PATENT DOCUMENTS

| 4,282,881 A | 8/1981 | Todd |
| 4,809,709 A | 3/1989 | Brooks |

(Continued)

FOREIGN PATENT DOCUMENTS

| CA | 2166710 | 5/1996 |
| EP | 0761162 | 3/1997 |

(Continued)

OTHER PUBLICATIONS

International Search Report and Written Opinion for PCT/US2013/075367 dated Mar. 20, 2014 (12 pages).

(Continued)

*Primary Examiner* — Nathan R Price
*Assistant Examiner* — Anh Bui
(74) *Attorney, Agent, or Firm* — Mueting, Raasch & Gebhardt, P.A.

(57) ABSTRACT

Methods and extracorporeal blood treatment systems reposition a diaphragm of a pressure measurement apparatus (e.g., a pressure pod apparatus of an extracorporeal blood set) by, for example, controlling an air pump apparatus to move the diaphragm toward a target measuring position based on a calculated target air volume (e.g., wherein the calculated target air volume is representative of the air volume necessary to move the diaphragm to the target measuring position based at least on a monitored air pressure). For example, after the diaphragm is bottomed out or topped out, as air is added to or removed from the transducer (Continued)

side cavity of a pressure pod apparatus, the target air volume may be iteratively calculated until it is determined that the diaphragm is repositioned in the target measuring position.

20 Claims, 11 Drawing Sheets

(51) Int. Cl.
  *G01L 19/02* (2006.01)
  *G01L 19/00* (2006.01)
  *G01L 19/14* (2006.01)
  *A61M 1/34* (2006.01)

(52) U.S. Cl.
  CPC ........ *A61M 1/3609* (2014.02); *A61M 1/3639* (2013.01); *A61M 1/3641* (2014.02); *G01L 19/0023* (2013.01); *G01L 19/0046* (2013.01); *G01L 19/02* (2013.01); *G01L 19/142* (2013.01); *A61M 2205/07* (2013.01); *A61M 2205/15* (2013.01); *A61M 2205/3331* (2013.01); *A61M 2205/3358* (2013.01); *A61M 2205/50* (2013.01); *A61M 2205/502* (2013.01); *A61M 2205/505* (2013.01)

(56) References Cited

U.S. PATENT DOCUMENTS

| | | | |
|---|---|---|---|
| 5,257,630 A | 11/1993 | Broitman | |
| 5,722,399 A * | 3/1998 | Chevallet | ............ A61M 1/3639 600/485 |
| 5,795,317 A | 8/1998 | Brierton | |
| 6,024,704 A | 2/2000 | Meador | |
| 6,044,691 A | 4/2000 | Kenley | |
| 6,280,406 B1 | 8/2001 | Dolecek | |
| 6,526,357 B1 | 2/2003 | Soussan | |
| 6,821,432 B2 | 11/2004 | Metzner | |
| 7,748,275 B2 | 7/2010 | Kouda | |
| 8,087,303 B2 | 1/2012 | Beavis | |
| 8,092,414 B2 | 1/2012 | Schnell | |
| 8,960,010 B1 | 2/2015 | Crnkovich | |
| 9,393,358 B2 | 7/2016 | Gronau | |
| 10,004,837 B2 | 6/2018 | Gronau | |
| 2001/0002552 A1 | 6/2001 | Vinci | |
| 2007/0061089 A1 | 3/2007 | Liu | |
| 2008/0202234 A1 * | 8/2008 | O'Neill | ................... G01C 5/06 73/384 |
| 2010/0275673 A1 | 11/2010 | Kouda | |
| 2016/0101226 A1 | 4/2016 | Beiriger | |
| 2017/0143886 A1 | 5/2017 | Wilt | |
| 2018/0024022 A1 | 1/2018 | Beden | |
| 2018/0093033 A1 | 4/2018 | Crnkovich | |

FOREIGN PATENT DOCUMENTS

| | | |
|---|---|---|
| EP | 1078642 | 2/2001 |
| EP | 2009415 | 12/2008 |
| EP | 2233164 | 9/2010 |
| FR | 2834560 | 7/2003 |
| JP | 2010 125131 | 6/2010 |
| WO | WO 0148451 | 7/2001 |
| WO | WO 2008/148649 | 12/2008 |

OTHER PUBLICATIONS

International Preliminary Report on Patentability for PCT/US2013/075367 dated Jul. 2, 2015 (8 pages).

* cited by examiner

TARGET VOLUME BASED DIAPHRAGM REPOSITIONING FOR PRESSURE MEASUREMENT APPARATUS

CROSS-REFERENCE

This application is the U.S. National Stage Application of International Application No. PCT/US2013/075367, filed Dec. 16, 2013 and published in English on Jun. 26, 2014 as International Publication No. WO 2014/099767 A1, which claims the benefit under 35 U.S.C. 119(e) of U.S. Provisional Application Ser. No. 61/739,973, filed Dec. 20, 2012; all of which are incorporated herein by reference in their entirety.

BACKGROUND

The disclosure herein relates to pressure measurement apparatus, such as, for example, used in extra-corporeal blood treatment. More particularly, the disclosure relates to diaphragm repositioning in such pressure measurement apparatus (e.g., repositioning the diaphragm of a pressure pod such that valid pressure readings are obtainable).

Extracorporeal blood sets, for example, are used in a variety of medical procedures to treat patients, such as, the infusion of drugs, dialysis, continuous renal replacement therapy (CRRT), extracorporeal membrane oxygenation (ECMO), etc. Reducing cost while maintaining safety and accuracy are of concern in today's healthcare environment. Reducing the number of tasks a user must perform and/or monitoring tasks performed such that the tasks are completed correctly, reduces the cost of operation and increases the quality of health care.

In many extracorporeal blood sets (e.g., disposable blood sets) provided, for example, for use in therapy systems, pressure pods are used to separate the liquid/blood filled disposable extracorporeal circuit from an electronic pressure sensor of the system by preventing liquid ingress and contamination while enabling the transfer and measurement of pressure. Such pressure pods may include a pressure transducer side separated from a fluid flow side by a diaphragm. In one or more configurations, for example, the pressure transducer side of the pressure pod is filled with air in a sealed space providing isolation (e.g., electrical isolation) thereof from the fluid flow side and a medium for the transfer of pressure from the fluid flow side to the pressure transducer side of the pressure pod, e.g., the compression of air. For example, the diaphragm which separates the pressure transducer side from the fluid flow side of the pressure pod may be flexible and oversized to ensure none of the force exerted by the pressure on the diaphragm in the extracorporeal blood circuit is lost to the tension or compression of the diaphragm. Further, for example, the pressure pod (e.g., via the pressure transducer side of the pressure pod) may be operatively connected by tubing (e.g., air filled) to a pressure transducer for sensing pressure at a distance away from the pressure pod (e.g., a pressure transducer located in a system housing upon which the extracorporeal blood set is mounted or a system to which the extracorporeal blood set is connected).

For example, a disposable extracorporeal blood set connectable to a treatment system (e.g., mounted on a system housing and connected to one or more pressure transducers therein) may contain multiple pressure pods. Each pressure pod may contain a diaphragm that separates a liquid (e.g., blood in the fluid side of the pressure pod) from an air cavity (e.g., on the transducer side of the pressure pod) and which is configured to fit into a pressure sensor or pod receptacle of the system (e.g., a connection apparatus for mounting the pressure pod on a dialysis unit). The pressure pods and pressure transducers (e.g., transducers inside the control unit or system housing, such as a dialysis unit) enable noninvasive pressure monitoring of the liquid (e.g., blood), since the liquid never comes into contact with the actual pressure transducer. A pressure pod receptacle may be used to provide connection between the pressure pods and the pressure transducers within the system housing. For example, the pressure pods may be manually attached to the pressure pod receptacle by a user each time a new disposable blood set is installed.

Since air is compressible and follows the ideal gas law under low pressures which exist in the extracorporeal blood circuit, the diaphragm position is a function, for example, of the atmospheric pressure, the volume of air in the closed space encompassing the air volume of the pressure transducer, any tubing volume between the pressure transducer and pressure pod, the elasticity of the tubing, and the volume of air in the pressure pod. As the circuit pressure increases and decreases in the liquid path during therapy such as dialysis, the position of the diaphragm will change accordingly. For example, under negative pressure, the flexible membrane, e.g., the diaphragm, will deflect towards the blood portion, e.g., liquid flow side, of the pressure pod and, for example, during positive pressure, the flexible membrane will flex toward the air side or pressure transducer side of the pressure pod.

However, if there is too little or too much air volume in the pressure transducer side, i.e., the air side, of the pressure pod due to, for example, a leak, a change in temperature, a change in blood pressure, or a change in atmospheric pressure, the potential exists for the flexible diaphragm to touch the pod casing on the liquid flow side of the pressure pod (e.g., top out) or come under tension (e.g., due to the slack in the flexible diaphragm being used) and bottom out (e.g., touch the pod casing on the transducer side of the pressure pod) resulting in an incorrect pressure reading because the true circuit pressure is no longer being transmitted. Conventionally, medical device systems have overcome such limitations by, for example, alerting the user to changes in pressure or at set periods of time to request the user to check the diaphragm position and/or to enable a repositioning of the diaphragm by the user. Such a check and/or reposition procedure takes user time and also may momentarily disable pressure measurement during the procedure (e.g., during therapy being provided to a patient).

For example, during a software initiated periodic check and/or reposition procedure carried out by a user (e.g., see the Open Loop Diaphragm Repositioning Sequence described herein), the diaphragm position may be adjusted back to a centered measuring position by infusing air to or withdrawing air from the enclosed space on the transducer side of the pressure pod. The trapped volume of air within the pressure pod is a known volume and by flexing the diaphragm under positive and negative pressure, the extension limits of the flexible diaphragm may be found by examining the rate of the change in pressure. For example, when the diaphragm deflection is halted due to tension or due to the diaphragm coming into contact with the sides of the pod (e.g., topped out or bottomed out on the pod casing), the rate of change of pressure will dramatically increase because the compliance of the chamber decreases, where compliance is measured in terms of pressure change per change in volume of air. Once both the positive and negative extension limits are determined, the centered measuring position may be found by infusing a known volume of air into the closed system (e.g., by activating a valve and connecting a positive displacement air pump to the enclosed space on the transducer side of the pressure pod).

In other words, for example, a disposable extracorporeal blood set connectable to a therapy system (e.g., mounted on a system housing and connected to one or more pressure transducers therein), may contain multiple circular pressure pods. Each pressure pod may contain a diaphragm that separates a liquid (e.g. blood in the liquid side of the pressure pod) from an air cavity (e.g., on the transducer side of the pressure pod) and which is configured to fit into a pressure sensor housing on a control unit (e.g., a mating receptacle for mounting the pressure pod on a dialysis unit). The pressure pods and pressure transducers (e.g., inside the control unit, such as a dialysis unit) enable noninvasive pressure monitoring of the liquid (e.g., blood), since the liquid never comes into contact with the actual pressure transducer. However, for the sensor to yield valid pressure readings, the pressure pod diaphragm must stay in a center range of the pressure pod. This may be accomplished by using an air pump (e.g., of a pump system) to add air to or remove air from the pressure pod air cavity (e.g., on the transducer side of the pressure pod) such that the air pressure on the air side of the diaphragm (e.g., the transducer side of the pressure pod) is equal to the liquid pressure on the other side of the diaphragm (e.g., the liquid flow side of the pressure pod). This may be referred to as having the pod diaphragm "in the measuring position" (e.g., a target measuring position).

Two conventional methods that may be used to move the diaphragm to the centered position include an Open Loop Diaphragm Repositioning Sequence and a Research of Plateau Repositioning Sequence. For example, an Open Loop Diaphragm Repositioning Sequence may be performed as follows. Periodically, an air pump may be operated to either add or remove air such that the pressure transducer readings from a given pressure pod is increased or decreased by 100 mmHg. If the initial pressure difference between the air cavity pressure and liquid pressure is small, then the diaphragm should be pushed against one of the pressure pod walls (e.g., on the transducer side or the liquid flow side of the pressure pod). This is referred to as the diaphragm either being bottomed out (e.g., minimum air cavity volume) or topped out (e.g., maximum air cavity volume). Then the pump may be operated to add or remove air volume equal to ½ the total volume of the pod. If the diaphragm was either bottomed out or topped out, this should center the diaphragm in the pod. However, if the diaphragm was not actually bottomed out or topped out, then it will not be centered after the open loop diaphragm repositioning sequence. Numerous conditional checks (e.g., such as calculating the derivative of the pressure readings while the pump is adding or removing air) are done to determine success or failure of the open loop repositioning sequence. If these checks indicate a failure, then a Research of Plateau Test Sequence may be executed. If the checks indicate success, then the repositioning sequence for the given pod may be terminated.

The Research of Plateau Repositioning Sequence may be performed as follows. This sequence may be executed if automated checks indicate that the open loop diaphragm repositioning sequence failed. In this sequence, the air pump is again used to add/remove air to/from the pod air cavity (e.g., on the transducer side of the pressure pod). In this case, however, the derivative of the pressure transducer reading is calculated while the pump is adding/removing air at a constant rate. If the diaphragm is in the measuring range, then the pressure derivative magnitude will be small. When the diaphragm reaches either a bottomed out or topped out condition, however, the pressure derivative magnitude increases beyond a threshold, indicating that the diaphragm has reached one wall of the pressure pod. At that point, the pump direction may be reversed and continue to operate until the pressure derivative again exceeds a threshold indicating that the diaphragm has contacted the opposite wall of the pressure pod. The air pump may again be reversed to add or remove an air volume equal to half of the volume required to move the diaphragm from the initial pod wall contact to the opposite pod wall contact. The diaphragm should then be centered in the pod and pressure readings from the pressure sensor (e.g., pressure measurements) should be valid.

Further, for example, the position of the diaphragm may also be manually repositioned by a user. For example, based upon the user visually examining the position of the diaphragm, the user may infuse air or remove air from the system to center the diaphragm (e.g., the user may control the pump to infuse or remove air).

However, as mentioned herein, such processes (e.g., processes that, for example, request the user to check the diaphragm position at set periods of time) undesirably take user time to perform. Further, the dependence on pressure derivative calculations make the process sensitive to pressure sensor random noise and periodic pressure peaks resulting from, for example, peristaltic pumps used to pump liquids in a system where pressure measurements may be taken. Still further, heavy digital filtering may be required to reduce the resulting pressure derivative peaks to a level that does not cause false triggering of the various Open Loop Diaphragm Repositioning Sequence and Research of Plateau Repositioning Sequence tests. Such filtering may result in up to two seconds of latency in obtaining the filtered pressure and pressure derivative used in the repositioning sequence. Further, the repositioning sequence may take up to three minutes per pressure pod and may be repeated if the first attempt fails. During this time, therapy pressure monitoring using the pressure pod under test may not be available even though the patient therapy or treatment is continuing. Yet further, with two different sequences (e.g., Open Loop and Research of Plateau processes) being used, with decision criteria being used to decide whether to start the sequence by either adding or removing air, and with decision criteria being used to determine success or failure of either sequence, the algorithms for implementing the sequences may be complex.

SUMMARY

The present disclosure, in one or more embodiments, describes a target volume based pressure pod diaphragm repositioning algorithm that provides an automated sequence to center the diaphragm of one or more pressure pods (e.g., without needing to rely on a pressure derivative calculation). In one or more embodiments, the algorithm may use an air pump apparatus (e.g., an Automatic RePositioning System (ARPS) air pump) to remove air from the pressure pod air transducer side cavity and bottom out the pressure pod diaphragm (e.g., by pulling the air cavity pressure to a more negative value than any operating pressure expected for that pod). The air pump apparatus may then be commanded to add air into the pressure pod air transducer side cavity and the resulting pressure may be monitored to calculate the total volume of air to be added from the bottomed out position that will result in the diaphragm being in its target measuring position in the pod (e.g., this volume being the "target volume"). The actual volume of air being added by the air pump apparatus may be determined by monitoring the pump apparatus (e.g., monitoring the rotation of a pump apparatus that delivers a known amount of air for each rotation). For example, in one embodiment, when the actual amount of air delivered matches the calculated "target volume", then the diaphragm may be determined to be in its target measuring position and valid pressure readings may be obtained from a transducer associated with the pod pressure (e.g., pressure readings corresponding to the liquid pressure on the liquid or fluid side of the diaphragm).

In one or more embodiments, the air target volume calculations may be corrected for ambient atmospheric pressure effects (e.g., using an atmospheric pressure value from either an atmospheric pressure sensor of the system itself or a fixed value entered by a service technician when the device is set up at a specific location). Since the repositioning process need not depend on a calculated pressure derivative, it may be less sensitive to pressure sensor noise and peristaltic pump pressure peaks. In one or more embodiments, the algorithm may start from a topped out diaphragm position, and then air may be removed until the calculated target volume is reached using similar calculated target volume techniques. Further, for example, in one or more embodiments, the present disclosure may provide for the repositioning of multiple pressure pods by applying the target volume algorithm in a sequential manner to multiple pressure pods (e.g., using an electronically controlled valve system connected between the air pump apparatus and pressure pods.

One or more embodiments described herein may provide for one or more of the following advantages. For example, the lack of dependence on pressure derivative calculations may reduce algorithm sensitivity to pressure sensor random noise and periodic peristaltic pump pressure peaks. The pressure derivative, for example, may still be used as an independent verification of correct repositioning. Further, for example, digital filtering may be reduced (e.g., faster time constants may be used) thus reducing latency in the filtered pressure signal used in the repositioning process. Still further, for example, the maximum repositioning sequence time may be reduced since, in one or more embodiments, a single process sequence may be implemented versus the implementation of two different sequences (e.g., Open loop and Research of Plateau processes). Thus, the time that pressure monitoring is unavailable during therapy may be reduced. Yet further, for example, with implementation of a single process sequence versus two different sequences (e.g., Open loop and Research of Plateau processes), the diaphragm repositioning sequence may be simplified.

One exemplary embodiment of an extracorporeal blood treatment system according to the present disclosure may include a pressure measurement apparatus (e.g., a pressure pod apparatus that includes at least a pod body portion and a base body portion; and that further may include a diaphragm separating a fluid side cavity defined at least in part by the pod body portion from a transducer side cavity defined at least in part by the base body portion, wherein the fluid side cavity is in fluid communication with an inlet and an outlet). For example, the diaphragm may be displaceable from a target measuring position into the fluid side cavity towards the pod body portion and may be displaceable from the target measuring position into the transducer side cavity towards the base body portion. The system may further include an air pump apparatus coupled to the transducer side cavity via one or more connection elements to add air to or remove air from the transducer side cavity, at least one pressure transducer operatively coupled to the transducer side cavity to sense air pressure therein, and a controller operatively coupled to the air pump apparatus and the at least one pressure transducer to reposition the diaphragm to the target measuring position. For example, the controller may be configured to control the air pump apparatus to bottom out the diaphragm on the base body portion by removing air from the transducer side cavity and/or to top out the diaphragm on the pod body portion by adding air to the transducer side cavity, monitor the air pressure in the transducer side cavity sensed by the at least one transducer, calculate a target air volume required to move the diaphragm to the target measuring position based at least on the monitored air pressure, and control the air pump apparatus to add air to the transducer side cavity after the diaphragm is bottomed out to move the diaphragm toward a target measuring position based on the calculated target air volume or to remove air from the transducer side cavity after the diaphragm is topped out to move the diaphragm toward a target measuring position based on the calculated target air volume.

In one or more embodiments of the system, as air is added to or removed from the transducer side cavity, the controller may be configured to iteratively calculate the target air volume required to move the diaphragm to the target measuring position based at least on the monitored air pressure until the controller determines that the diaphragm is in the target measuring position based on a comparison of the calculated target air volume and a total amount of air added to or removed from the transducer side cavity.

A method (e.g., a pressure measurement method for an extracorporeal blood treatment system) according to the present disclosure may include providing a pressure measurement apparatus (e.g., a pressure pod apparatus including at least a pod body portion and a base body portion; and a diaphragm separating a fluid side cavity defined at least in part by the pod body portion from a transducer side cavity defined at least in part by the base body portion, wherein the fluid side cavity is in fluid communication with an inlet and an outlet). The diaphragm may be displaceable from a target measuring position into the fluid side cavity towards the pod body portion and may be displaceable from the target measuring position into the transducer side cavity towards the base body portion. Further, the method may include providing an air pump apparatus coupled to the transducer side cavity via one or more connection elements to add air to or remove air from the transducer side cavity, controlling the air pump apparatus to bottom out the diaphragm on the base body portion by removing air from the transducer side cavity or to top out the diaphragm on the pod body portion by adding air to the transducer side cavity, monitoring the air pressure in the transducer side cavity, and controlling the air pump apparatus to add air to the transducer side cavity after the diaphragm is bottomed out to move the diaphragm toward a target measuring position based on a calculated target air volume or to remove air from the transducer side cavity after the diaphragm is topped out to move the diaphragm toward a target measuring position based on the calculated target air volume (e.g., the calculated target air volume may be representative of the air volume necessary to move the diaphragm to the target measuring position based at least on the monitored air pressure). Further, for example, as air is added to or removed from the transducer side cavity, the target air volume may be iteratively calculated until it is determined that the diaphragm is repositioned in the target measuring position based on a comparison of the calculated target air volume and a total amount of air added to or removed from the transducer side cavity.

Further, in one or more embodiments of the system and/or method, the calculation of target air volume may be adjusted for atmospheric conditions. For example, the calculation of target air volume may be adjusted using a user input value representative of atmospheric pressure at a particular location or the calculation of target air volume may be adjusted using a value representative of atmospheric pressure measured by an atmospheric pressure sensor of the system.

Further, in one or more embodiments of the system and/or method, a controller may be configured to determine the total amount of air added or removed by monitoring rotation of an air pump apparatus which delivers a known amount of air per rotation and/or the controller may be configured to determine that the diaphragm is in the target measuring position when the amount of air added to or removed from the transducer side cavity meets or exceeds the calculated target air volume.

Still further, in one or more embodiments of the system or method, a controller may be configured to calculate the target air volume required to move the diaphragm to the target measuring position based at least on the monitored air pressure, an actual volume defined by the transducer side cavity desired to move the diaphragm to the target measuring position, and an actual volume defined by the one or more connection elements used to couple the air pump apparatus to the transducer side cavity of the pressure measurement apparatus (e.g., the one or more connection elements used to couple the air pump apparatus to the transducer side cavity may include one or more tubes, and, as such, the calculation of the target air volume may be based on a compliance of the one or more tubes).

Yet further, in one or more embodiments of the system or method, the pressure measurement apparatus may be provided as part of an extracorporeal blood set that includes a plurality of pressure measurement apparatus mountable on a system housing containing at least the controller and at least one pressure transducer corresponding to each of the plurality of pressure measurement apparatus. Further, a plurality of valves may be provided and a controller may be configured to operate a different valve for each of the plurality of pressure measurement apparatus mounted on the system housing to allow the diaphragm of each of the pressure measurement apparatus to be separately repositioned during different time periods. Further, for example, a controller may be configured to use air pressure measurements from a pressure transducer corresponding to a pressure measurement apparatus for therapy pressure monitoring prior to repositioning the diaphragm of the pressure measurement apparatus and may be configured to temporarily discontinue the use of the air pressure measurements from the corresponding pressure transducer for therapy pressure monitoring when the diaphragm is being repositioned.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
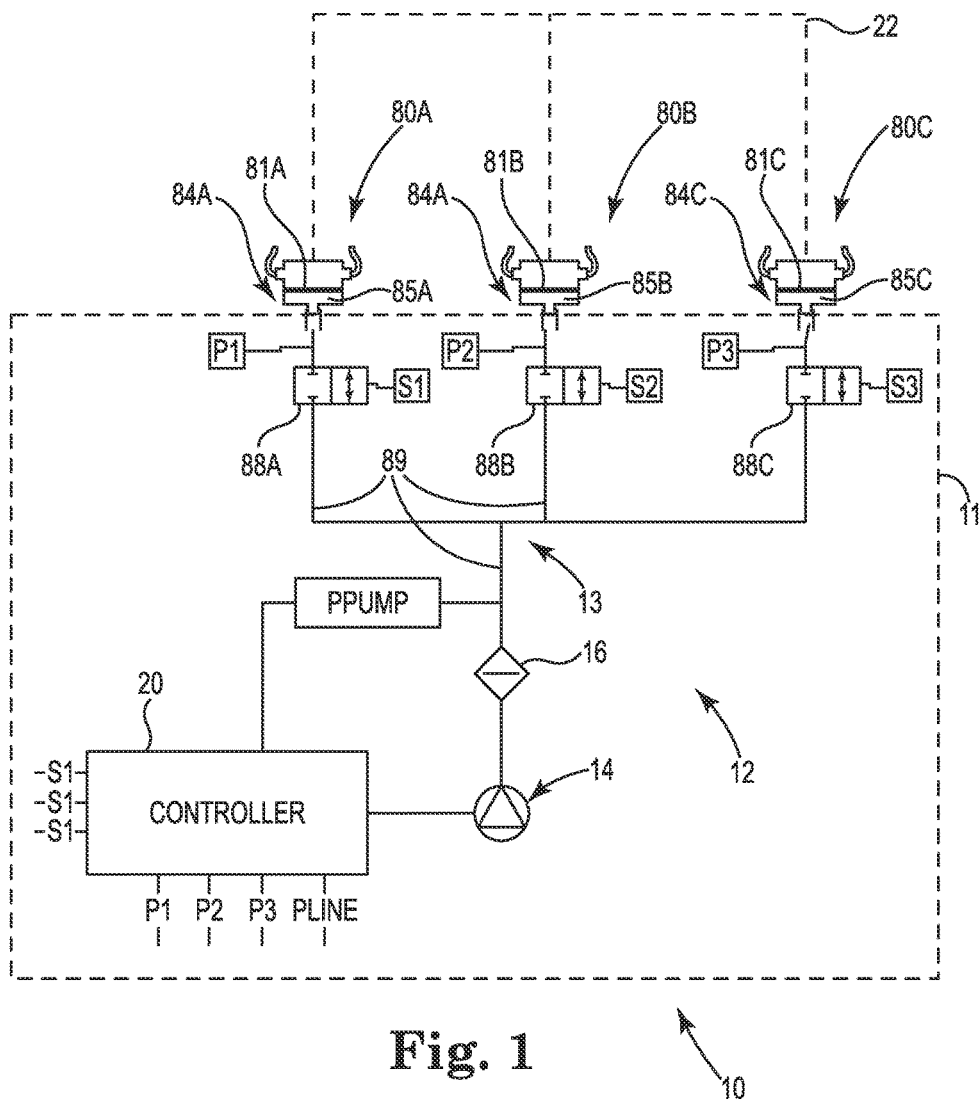
FIG. 1 is a block diagram showing a fluid processing system, such as shown in FIGS. 2-3, including a diaphragm repositioning system (e.g., to reposition a diaphragm of a pressure pod apparatus of an extracorporeal blood set connected to components of or within a system housing containing, for example, a controller and/or pressure transducer(s) of the fluid processing system).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods for use in repositioning a diaphragm, for example, of a pressure measurement apparatus (e.g., a pressure measurement apparatus including a pressure pod of an extracorporeal blood set connected to a fluid processing system, such as, e.g., an extracorporeal blood processing system) shall be described with reference to FIGS. 1-9. For example, in one or more embodiments, such systems and methods may use an air pump apparatus (e.g., an automatic repositioning system air pump (an ARPS pump)) and one or more pressure transducers of a fluid handling system to reposition the diaphragm of a pressure pod apparatus connected to a system housing of the fluid processing system based on a calculated target volume (e.g., a target volume calculated based on pressure measurements by a pressure transducer of the system, such as, for example, the pressure transducer used to measure pressures of flow through the pressure pod during a treatment or therapy being delivered by the system; which target volume may be calculated taking into consideration atmospheric conditions).

Figure 2:
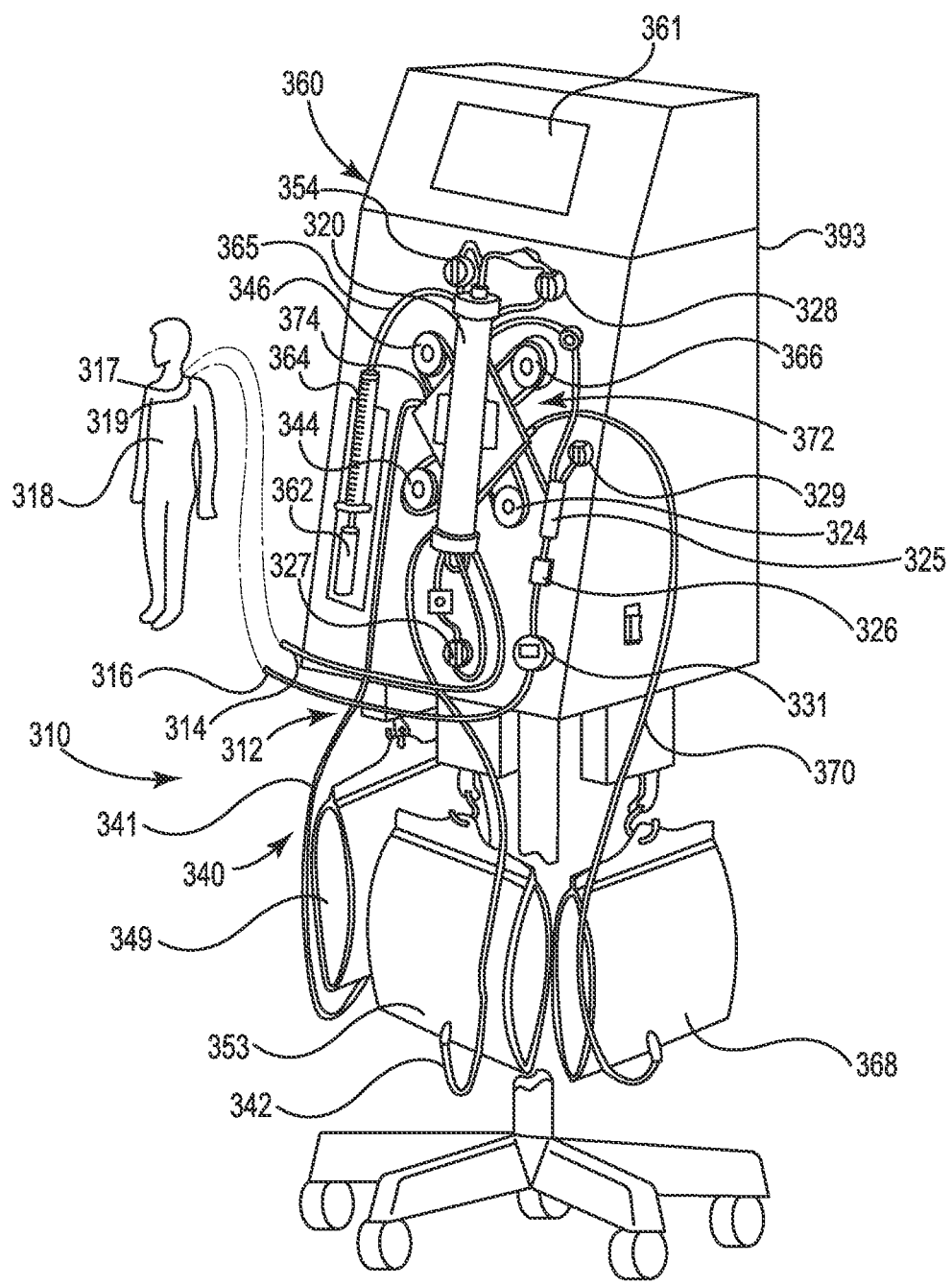
FIG. 2 is a perspective illustration of an exemplary fluid processing system that may include a diaphragm repositioning system such as shown generally in FIG. 1.
Figure 3:
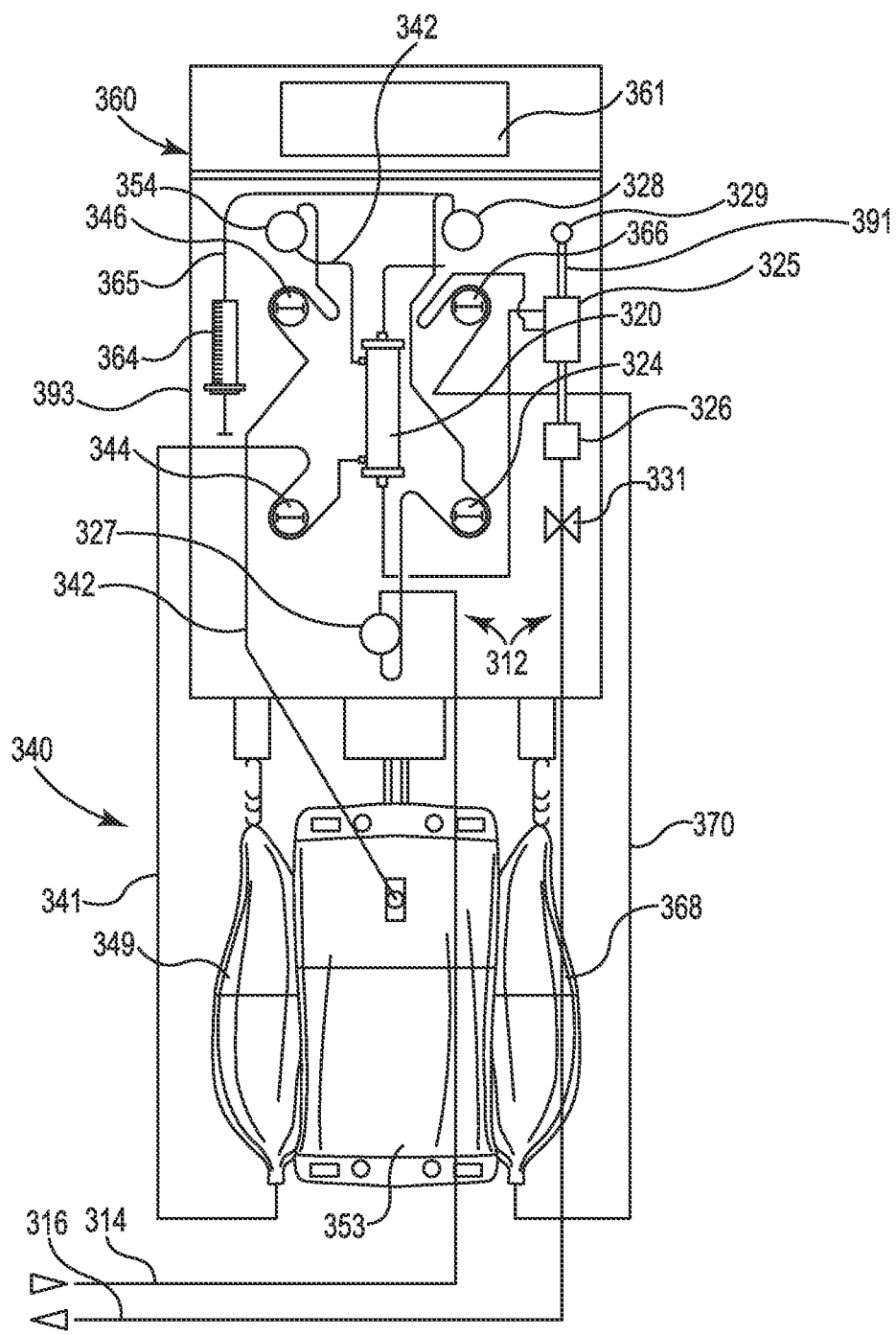
FIG. 3 is a front view of a portion of the exemplary fluid processing system shown in FIG. 2.

FIG. 1 shows a block diagram of an exemplary fluid processing system 10, such as an extracorporeal blood treatment system shown in FIGS. 2-3, that includes a diaphragm repositioning system 12 for repositioning one or more diaphragms of corresponding pressure measurement apparatus (e.g., a diaphragm 81A-81C of a corresponding pressure pod apparatus 80A-80C of an extracorporeal blood set 22) of the system 10 (e.g., which pressure pod apparatus 80A-80C may be connected to corresponding pressure transducers (e.g., P1-P3) located within system housing 11). For example, as shown in FIG. 1, the fluid processing system 10 may be an extracorporeal blood treatment system that includes system housing 11. The diaphragm repositioning system 12 may be used to reposition each of the diaphragms 81A-81C of corresponding pressure pod apparatus 80A-80C of the extracorporeal blood set 22 (e.g., a disposable blood set) to a target measuring position (e.g., a centered measuring position) such that, for example, valid pressure readings may be obtained during operation of the system 12 (e.g., during set up, during treatment or therapy, etc.).

The extracorporeal blood treatment system 10 includes an air pump apparatus 14, one or more pressure transducers (e.g., P1, P2, P3, and Ppump), and a controller 20 operatively coupled to the air pump apparatus 14 and the one or more pressure transducers (e.g., P1, P2, P3, and Ppump). The extracorporeal blood set (shown generally as reference number 22) may include a plurality of components (e.g., pressure pod apparatus 80A-80C, various lines or tubes, etc.) configured to be mounted on or coupled to the system housing 11 of the extracorporeal blood treatment system 10, and the present disclosure is not limited to any particular blood set and/or components thereof. However, for example, such components may be those used to obtain pressure measurements related to the flow of fluid (e.g., blood) through the lines or tubing of the extracorporeal blood set 22. For example, the extracorporeal blood set 22 may include pressure pod apparatus 80A-80C mountable on or which may be coupled to the system housing 11 of the fluid processing system 10. The pressure pod apparatus 80A-80C may each include a transducer side cavity 85A-85C, for example, operatively connected or connectable (e.g., via a port, via a tube which may be coupled to the port, etc.) to at least one of the one or more pressure transducers (e.g., P1, P2, P3, Ppump). Such pressure pod apparatus shall be described further herein.

One or more connection elements 13 may be used to connect the air pump apparatus 14, as well as the pressure transducers (e.g., P1, P2, P3, and Ppump), to the pressure pod apparatus 80A-80C (e.g., such connection elements may include mating receptacles, couplers, internal control components and/or fluid tubing system components, including components such as one or more tubes, one or more valves, filters, etc.). For example, the one or more connection elements 13 may include connection apparatus 84A-84C (e.g., mating receptacles including one or more ports, tubing connected to ports, etc.) to provide for the connection between the one or more pressure transducers (e.g., P1, P2, P3, and Ppump) contained in the system housing 11 to the one or more pressure pod apparatus 80A-80C of the extracorporeal blood set 22 when mounted on the system housing 11 (e.g., providing an air or fluid connection for use in sensing pressure). Further, the one or more connection components 13 may include tubing 89 (e.g., flexible tubing having a compliance associated therewith) to connect, for example, the pump apparatus 14 to the one or more pressure pod apparatus 80A-80C. One skilled in the art will recognize that such connection elements 13 will vary depending on the implemented system configuration and may not use one or more of the connection elements described herein and/or may use other connection elements not described herein. Such connection elements 13 have a defined volume associated therewith; which defined volume may change depending on the pressure of fluids (e.g., liquid or gas) provided therein. For example, the defined volume may be generally representative of the volume in the path connecting the pump apparatus 14 and pressure transducers (e.g., P1, P2, P3, and Ppump) to the pressure pod apparatus 80A-80C (e.g., to the transducer side cavity 85A-85C thereof).

The controller 20 is configured to control the air pump apparatus 14 to provide air to or remove air from (e.g., via at least one port of one or more ports of the connection apparatus 84A-84C) within at least a portion of the pressure pod apparatus 80A-80C (e.g., within the transducer side cavity 85A-85C thereof) of the extracorporeal blood set 22 when mounted on the system housing 11. The controller 20 may monitor air pressure at the ports (e.g., of the mating receptacles or connection apparatus 84A-84C), or in other words, may monitor the air pressure in the transducer side cavity 85A-85C of the pressure pod apparatus 80A-80C. Such monitoring may be implemented using the one or more pressure transducers (e.g., P1, P2, P3, and Ppump) and the monitored pressure may be used in calculating target volume for use in repositioning the diaphragm 81A-81C of one or more pressure pod apparatus 80A-80C of an extracorporeal blood set 22 to a target measuring position (e.g., such that valid pressure readings may be obtained, for example, during operation or treatment).

As described further herein, for example, in one or more embodiments, under control and/or execution, of controller 20, a target volume-based pressure pod diaphragm repositioning algorithm provides an automated sequence to reposition (e.g., center) the diaphragm 81A-81C of each pressure pod apparatus 80A-80C to a target measuring position. For example, the air pump apparatus 14 may be controlled to either bottom out the diaphragm (e.g., one of diaphragms 81A-81C) by removing air from the transducer side cavity of a pressure pod apparatus (e.g., one of pressure pod apparatus 80A-80C), or topping out the diaphragm by adding air to the transducer side cavity. With the air pressure in the transducer side cavity (e.g., one of transducer side cavities 85A-85C) being monitored, a target air volume required to move the diaphragm to the target measuring position may be calculated based on at least the monitored air pressure (e.g., the calculated target air volume may also be based on the volume defined by the pressure pod (for example, one half of the pressure pod), the volume defined by the connection elements (for example, the volume of the path between the pump apparatus and the pressure pod), the compliance of one or more connection elements, atmospheric pressure, etc.)

The air pump apparatus 14 may then be controlled to add air to the transducer side cavity (e.g., one of transducer side cavities 85A-85C) after the diaphragm (e.g., one of diaphragms 81A-81C) is bottomed out to move the diaphragm toward the target measuring position based on the calculated target volume or to remove air from the transducer side cavity (e.g., one of transducer side cavities 85A-85C) after the diaphragm (e.g., one of diaphragms 81A-81C) is topped out to move the diaphragm toward a target measuring position based on the calculated target volume. For example, as air is added to or removed from the transducer side cavity, the controller 20 may be configured to iteratively calculate the target air volume required to move the diaphragm to the target measuring position based on the continual monitoring of the pressure in the transducer side cavity (e.g., which calculated target volume may take into consideration atmospheric conditions) until the controller 20 determines that the diaphragm is in the target measuring position based on a comparison of the calculated target volume being iteratively calculated and a total amount of air being added to or removed from the transducer side cavity (e.g., which may be determined by monitoring the air pump apparatus). Such a comparison is shown graphically in FIG. 9 and shall be described herein in connection with a more detailed description of an exemplary repositioning process.

The diaphragm repositioning functionality described herein may be used in any fluid processing systems that would benefit therefrom. For example, exemplary systems that may benefit from such functionality include systems, generally referred to as dialysis systems. The general term dialysis as used herein includes hemodialysis, hemofiltration, hemodiafiltration, hemoperfusion, liver dialysis, and therapeutic plasma exchange (TPE), among other similar treatment procedures. In dialysis generally, blood is taken out of the body and exposed to a treatment device to separate substances therefrom and/or to add substances thereto, and is then returned to the body. Although extracorporeal blood treatment systems capable of performing general dialysis (as defined above, including TPE) and using diaphragm repositioning shall be described herein with reference to the exemplary extracorporeal blood treatment system of FIGS. 2-3, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular fluid processing system.

In the perspective and partial front views of FIGS. 2-3, the exemplary extracorporeal blood treatment system 310 that may implement diaphragm repositioning as described herein generally includes a blood tubing circuit 312 having first and second tubing segments 314 and 316 which are both connected to the vascular system of a patient 318 via access and return devices 317 and 319, respectively. Devices 317 and 319 may be cannulas, catheters, winged needles or the like as would be understood by one skilled in the art. Tubing segments 314 and 316 are also connected to a filtration or processing unit 320. In dialysis, filtration unit 320 is a dialyzer, which is also often referred to as a filter. In TPE, it may also be referred to as a plasma filter. In this exemplary system 310, a peristaltic pump 324 is disposed in operative association with the first tubing segment 314. Numerous other component devices of blood circuit 312 are also included such as, for example, pressure sensors 327 and 328. Such pressure sensors 327 and 328 may be configured as described herein and the diaphragms thereof may be repositioned to a target measuring position as described herein, for example, during setup and/or operation of system 310.

Also shown in FIGS. 2-3 is the processing fluid or filtrate side of system 310 which generally includes a processing fluid circuit 340 having first and second processing fluid tubing segments 341 and 342. Each of these tubing segments is connected to the filtration unit 320. In these FIGS. 2-3, a respective fluid pump 344, 346 is operatively associated with each of these tubing segments 341 and 342. First tubing segment 341 is also connected to a processing fluid source (e.g., fluid bag 349) which may include electrolytes premixed therein. Second tubing segment 342 is connected to a waste collection device (e.g., a waste container such as a bag 353). A pressure sensor 354 may also be disposed in second dialysis fluid tubing segment 342 (e.g., pressure sensor 354 may be configured as described herein and the diaphragm thereof repositioned as described herein, for example, during setup and/or operation of system 310).

FIGS. 2-3 show a system which is common as a basic model for numerous dialysis procedures including TPE. Additional fluid lines, circuits, and components may be added (or deleted) to increase treatment options. Further, as shown in FIGS. 2-3, the system 310 includes an extracorporeal blood control apparatus 360 which provides numerous treatment options which are controlled and/or monitored via the control/display screen 361 (e.g., a control apparatus or controller provided in a system housing 393). Touchscreen controls may be incorporated herewith and/or other conventional knobs or buttons (not shown) may be used. Other and more detailed information regarding an example apparatus 360 may be found in U.S. Pat. Nos. 5,679,245; 5,762,805; 5,776,345; and U.S. Pat. No. 5,910,252; inter alia.

A general dialysis treatment procedure as performed, for example, with an apparatus described with reference to FIGS. 2-3 will be generally described for exemplary purposes only. First, blood is removed from the patient 318 via access device 317 and flows through access line 314 to the filter 320. Filter 320 processes this blood according to a selected one or more of a number of extracorporeal blood treatment protocols (e.g., selected and controlled via screen interface 361 of control apparatus 360) and then returns the processed or treated blood to the patient 318 through return line 316 and return device 319 inserted in or otherwise connected to the vascular system of the patient 318. The blood flow path to and from the patient 318, which includes the access device 317, the access line 314, the filter 320, as well as the return line 316 and return device 319 back to the patient, forms the blood flow circuit 312.

The pressure sensors may be used to sense various pressures in the system 310. For example, the pressure sensor 327 (e.g., including an access pressure pod apparatus) may be connected in the access line 314 and allow the fluid pressure in the access line 314 to be monitored and the second pressure sensor 328 (e.g., including a filter pressure pod apparatus) may be connected in the blood circuit 312 between the first pump 324 and the blood entrance into the filter 320 and may be used to detect and monitor the pressure of the blood supplied to the entrance of the filter 320.

The system 310 may further include a deaeration chamber 325 in the return line to provide a conveyance path that operates like a vortex to propel air out of the blood. Post-filter replacement solution may be added into the deaeration chamber on the top of the blood to prevent an air/blood interface. A deaeration chamber monitor line 391 connects the deaeration chamber 325 to an internal pressure transducer within the system housing 393 using a connection apparatus, such as, for example, a return pressure port 329. This enables return pressure monitoring, and removal of air from the deaeration chamber, if needed. A return clamp 331 connected in the blood circuit 312 selectively allows or terminates the flow of blood through the blood circuit 312 (e.g., return clamp 331 may be activated whenever air is detected in the blood by bubble detector 326). Further, a pump 362 may be connected to an anticoagulant container 364 to deliver anticoagulant through an anticoagulant line 365 to the blood in tubing segment 314 and a pump 366 may deliver replacement fluid from a replacement fluid container or bag 368 through a replacement fluid line 370.

The secondary flow circuit 340 is also shown in FIGS. 2-3 as it interacts with filter 320. The secondary flow circuit 340 is connected to the secondary chamber of filter 320. Matter extracorporeally removed from the blood is removed from the secondary chamber of filter 320 through the outlet tubing segment 342 of the secondary flow circuit 340, and matter extracorporeally added to the blood is moved into filter 320 through inlet tubing segment 341 of the secondary flow circuit 340. The secondary flow circuit 340 may generally include the fluid source such as bag 349, inlet fluid line 341, third peristaltic pump 344, the secondary chamber of the filter 320, a waste fluid line 342, pressure sensor 354, fourth pump 346, and the waste collection device such as container 353. The source fluid bag 349 may contain a sterile processing fluid, generally isotonic to blood, into which blood impurities will diffuse through the semi-permeable membrane of the filtration unit 320. The pump 344 is connected in inlet fluid line 341 for delivering processing fluid from the processing fluid source 349 into an entrance to the filter 320. The waste collection container 353 is provided to collect or receive matter from the blood transferred across the semipermeable membrane in filter 320 and/or to receive the used processing fluid after it has passed through the filter 320. The fourth pump 346 is connected to the waste collection line 342 for moving body fluid from the filter 320 into the waste collection container 353. The pressure sensor 354 may also be located in the waste collection line 342 for the purpose of monitoring the pressure in the secondary chamber of filter 320.

The filtration unit 320, the flow tubing lines, and the other components in the primary and secondary flow circuits 312 and 340 described herein (with the exception, for example, of the pumps and perhaps a few other items) may be formed as an integral, replaceable unit (e.g., an extracorporeal blood set). An example of such an integral replaceable unit is described in greater detail in U.S. Pat. No. 5,441,636 entitled Integrated Blood Treatment Fluid Module (see also, U.S. Pat. No. 5,679,245, entitled Retention Device for Extracorporeal Treatment Apparatus). The diaphragm repositioning algorithms described herein may be used to reposition the diaphragm of one or more pressure pod apparatus of such an extracorporeal blood set to a target measuring position.

As can generally be appreciated from FIGS. 2-3, the integrated tubing and filter module (identified by the reference numeral 372), or extracorporeal blood set, includes the filter 320 and all the tubing and related components described above which are connectable to apparatus 360. For example, the filter and tubing may be retained on a plastic support member 374 which is, in turn, connectable to apparatus 360 (e.g., connectable to the system housing 393 of the apparatus 360). When in the operative position connected to apparatus 360, flexible fluid conducting tubing lines to and from the filtration unit 320 are held in operative, pump communicative loops for operative contact with the peristaltic pumping members of the pumps 324, 344, 346 and 366 to cause the fluid to flow through the primary (blood) and secondary (processing fluid) circuits 312 and 340. Module 372, including filter 320 and all the tubing lines and associated flow components may be disposable after use. The peristaltic pumping members of pumps 324, 344, 346, and 366 may be fixedly disposed on apparatus 360 (without the disposable tubing loop components) and may be re-usable. In general, electrical, mechanical, or electromechanical components are also fixedly disposed in or on apparatus 360 (e.g., connectable to the system housing 393 of the apparatus 360). Examples of such components include the display screen 361 (e.g., a touchscreen), the bubble detector 326, line clamps 331 and connection apparatus for coupling to the transducer side portions of pressure pod apparatus used to implement pressure sensors 327, 328, and 354 as is described herein.

Measurements by the pressure sensors 327, 328 and 354 may be used for one or more various control functions (e.g., used by the apparatus 360 in internal monitoring to make internal decisions and/or automatic adjustments to modify fluid flow parameters). The present disclosure is not limited in the manner the pressure sensor measurements are used by the system in which they are present.

Figure 4:
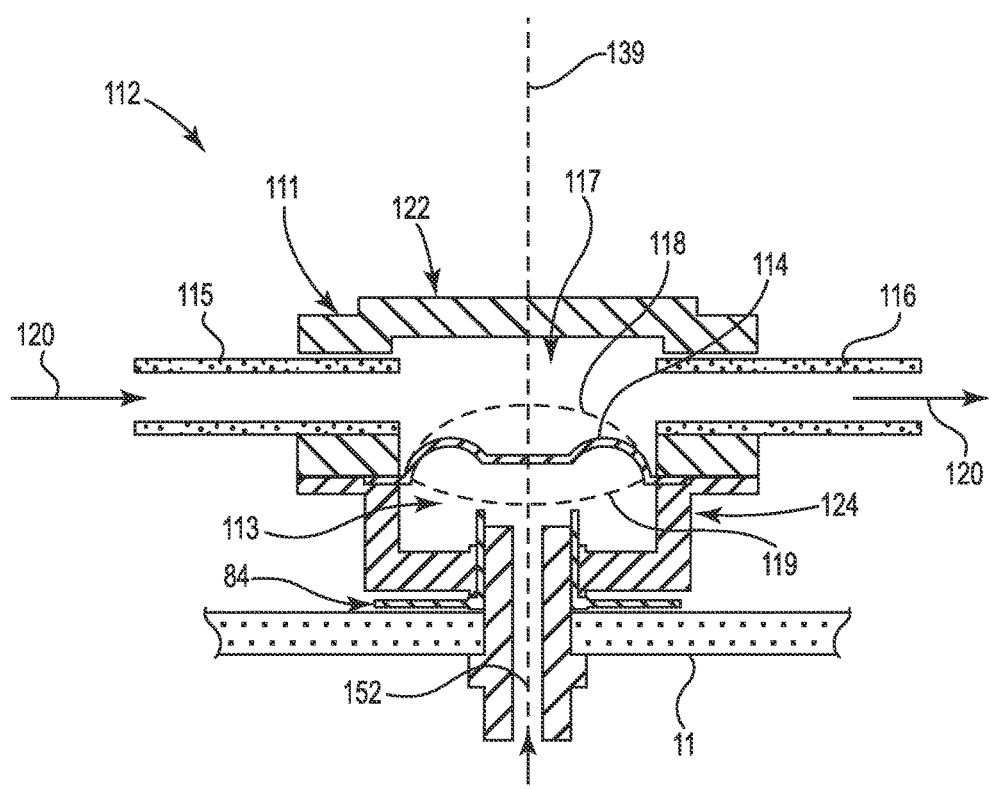
FIG. 4 is a cross-section view of an exemplary pressure pod apparatus mounted on a system housing which may be used in a system, for example, such as shown generally in FIGS. 1-3.

One or more of the pressure sensors 327, 328, and 354 may be provided with use of a pressure pod apparatus of a diaphragm type as described herein, for example, with reference to FIGS. 1, 4, and 5A-5C. One or more of the pressure sensors 327, 328, and 354 used may be separated into two distinct portions because the tubing segments 314, 316 and 342, and all other flow components which come into contact with blood and/or blood waste products are, at least in one embodiment, disposable. As such, at least the blood side components of these pressure sensors (e.g., the pressure pod apparatus 112 of each sensor as shown in FIG. 4) are thus also, at least in one embodiment, disposable (e.g., part of extracorporeal blood set 372). The electrical transducers are generally expensive and thus it is desirable that they be incorporated into apparatus 360; and thus, are reusable.

FIG. 4 is an illustrative diagram showing a removable pressure pod apparatus 112 (e.g., equatable to pressure pod apparatus 80A-80C shown in FIG. 1) coupled to system housing 11 (e.g., a system housing that contains one or more pressure transducers, a controller, valves, tubing, etc., such as housing 393 of FIGS. 2-3). Connection apparatus (or point of connection) between the pressure pod apparatus 112 and the system housing 11 (including connection to components therein) is shown generally as connection apparatus 84 in FIG. 4 (e.g., such connection apparatus may be similar to that used to mount pressure pod apparatus 412 in mating receptacle 545 of connection apparatus 540 shown in FIGS. 5-6, may include tubing from the transducer side cavity connectable to a port of the system, may be associated with apparatus 360 shown and described with reference to FIGS. 2-3, etc.).

In one or more embodiments, the pressure pod apparatus 112 may include a pressure pod body 111 that includes at least a pod body portion 122 and a base body portion 124 (e.g., a pressure pod body that may be coupled in a mating receptacle). As shown in the exemplary embodiment of FIG. 4, a diaphragm 114 (e.g., a flexible membrane) separates the liquid side cavity 117 defined at least in part by the pod body portion 122 from the transducer side cavity 113 defined at least in part by the base body portion 124. The liquid side cavity 117 is in fluid communication with an inlet 115 and an outlet 116 (e.g., through which liquid flows as indicated by arrows 120). The diaphragm 114 is displaceable from a centered measuring position (e.g., along axis 139) into the liquid side cavity 117 towards the pod body portion 122 as shown by dashed line 118 and is displaceable from the centered measuring position (e.g., along axis 139) into the transducer side cavity 113 towards the base body portion 124 as shown by dashed line 119. In other words, the flexible diaphragm 114 may flex as generally shown by positions 119 and 118.

As shown in the exemplary embodiment of FIG. 4, when in use, liquid may flow within the extracorporeal circuit between the inlet 115 and the outlet 116 of the pressure pod apparatus 112. The pressure of the liquid in liquid side cavity 117 flexes the diaphragm 114 until the pressure or force on both sides of the diaphragm 114 equalize. The flexible diaphragm 114 expands and contracts based upon the pressure exerted in the liquid side cavity 117 and the mass of gas in the connected tubing and transducer side cavity 113 (e.g., air cavity), atmospheric pressure, and temperature. For example, to measure the pressure exerted by the fluid (e.g., liquid such as blood) in liquid side cavity 117, a pressure transducer is connected through a series of tubes/valves to the transducer side cavity 113 (e.g., via a port defining a channel 152 extending through the connection apparatus 84). For example, such connection tubes used for connecting the pressure transducer to the transducer side cavity 113, or other connection tubing described or used herein, may be made from a polymer material suitable for preventing leakage in the pressure range of −700 to 700 mmHg.

In other words, for example, as shown in FIGS. 1 and 4, a pressure sensor with disposable components may include a disposable portion such as the pressure pod apparatus 112 which includes the pressure pod body 111 (e.g., a rigid, plastic casing sometimes referred to as a "pod"). The pressure pod apparatus 112 includes the diaphragm 114 disposed therein separating the pod body 111 into two fluid-tight compartments or cavities 117 and 113. The inlet 115 and the outlet 116 open into cavity 117 to allow liquid to flow into and through the cavity 117 (also referred to herein as the liquid side cavity). The other cavity 113 on the opposing side of the diaphragm 114 has at least one access point (e.g., generally only one access point) to allow for fluid communication therewith (e.g., for communication of a dry gas such as air with the cavity 113 (although wet/wet transducers may also be usable with the pressure pod apparatus 112)). This cavity 113 is also referred to herein as the transducer side cavity or compartment because a transducer is in pressure-sensing communication with the air (e.g., a dry gas) on this transducer side of diaphragm 114. As used herein, air, gas, and dry gas are used interchangeably.

At least in one embodiment, the pressure pod apparatus 112 including the diaphragm 114 is the disposable part of the pressure sensor (e.g., pressure sensor 327, 328, and 354). For example, when the pressure pod apparatus 112 is used with apparatus 360, apparatus 360 may include a corresponding mating receptacle (e.g., as part of a connection apparatus) in and/or to which each disposable pod apparatus 112 is connected putting the transducer side cavity 113 into fluid communication with, for example, a corresponding pressure transducer disposed in the apparatus 360, and simultaneously putting it in fluid communication with internal control components/fluid tubing system connected to an air pump apparatus (e.g., pump 14).

Liquid flowing through the fluid side cavity 117 of such a pressure pod apparatus 112 has an inherent fluid pressure which acts on the diaphragm 114 by moving it. When the diaphragm moves, the diaphragm either compresses or allows expansion of the fluid/dry gas in the transducer side cavity 113 (e.g., on the transducer side of the diaphragm 114). The pressure of the compressed or expanded fluid is sensed by the corresponding pressure transducer inside the control apparatus 360 (e.g., such as one of pressure transducers P1-P3 shown generally in FIG. 1). The pressure transducer converts the sensed pressure to an electrical signal which is sent to a controller, such as controller 20 shown in FIG. 1 (e.g., an electrical microprocessing unit in control apparatus 360 for analysis of the signals or for interpretation of the signal as a pressure value), which may then process the signal for display, storage or use by software (or hardware) for calculations (e.g., calculated target volume), or for carrying out any desired functionality (e.g., diaphragm repositioning).

The connection apparatus 84 of FIG. 1 (which is a generalization of connection apparatus 84A-84C as shown in FIG. 1), for example, may be of any suitable configuration for use in coupling with the pressure pod apparatus 112 and putting the transducer side cavity 113 into fluid communication with, for example, a pressure sensing transducer (e.g., a pressure sensing transducer disposed in the apparatus 360 coupled by one or more tubes, one or more valves, or any other connection elements). For example, such pressure pod apparatus 112 and mating connection apparatus (e.g., receptacles) may include configurations like those shown in FIGS. 5-6. However, any suitable configuration of the pressure pod apparatus and connection apparatus may be used.

At least in one or more embodiments, the connection apparatus 84 includes retention structure for coupling to and retaining one or more portions of the pressure pod apparatus 112 therein (e.g., maintaining the pressure pod apparatus in a stable fixed position, but still being removable from the receptacle). Further, for example, such connection apparatus may provide a port to connect the transducer side cavity 113 to a pressure transducer (e.g., one of P1-P3 shown generally in FIG. 1) contained in the system housing 11 when the pressure pod body 112 is mounted on the system housing 11 by the connection apparatus 84.

In other words, the pressure pod apparatus 112 may be of one or more various configurations. For example, the pod body 111 may take any shape as long as a diaphragm 114 separates the liquid side cavity 117 from the transducer side cavity 113 and permits effective transfer of pressure from the liquid flow in liquid side cavity 117 to transducer side cavity 113. For example, in one or more embodiments, the pressure pod body 111 may be formed of one or more components or portions thereof sealed together or may be a unitary structure. For example, the pod body portion 122 may be a separate body component having a surface sealed against a separate base body portion 124 and clamping the diaphragm 114 therebetween. Further, the pressure pod body 111 may be formed of any suitable material such as a polymer (e.g., polyvinyl chloride, polycarbonate, polysulfone, etc.).

Figure 5A:
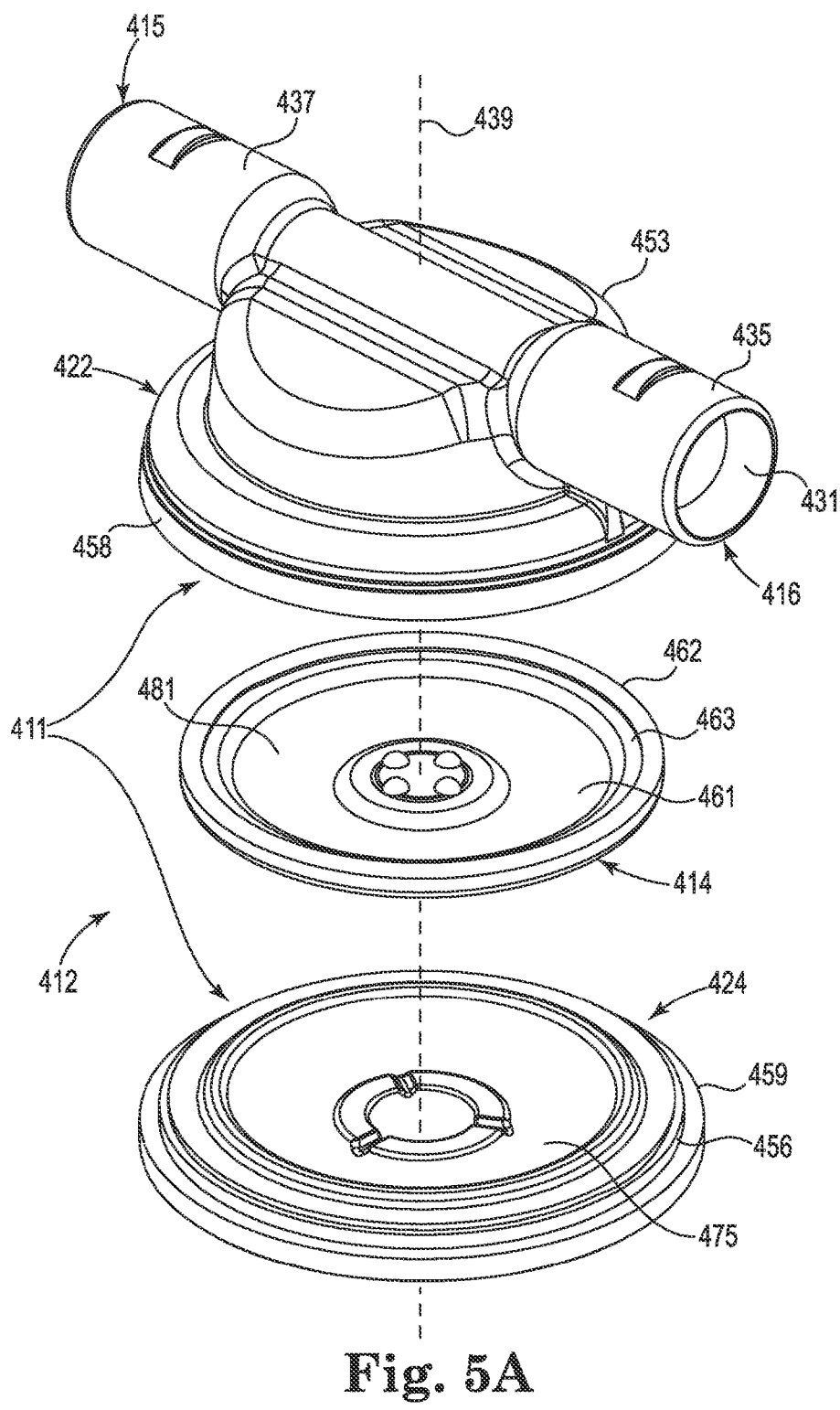
FIGS. 5A-5C show an exploded top perspective view, an exploded bottom perspective view, and a cut-away or cross-section perspective view of an exemplary pressure pod apparatus, such as generally shown in FIG. 4.
Figure 5B:
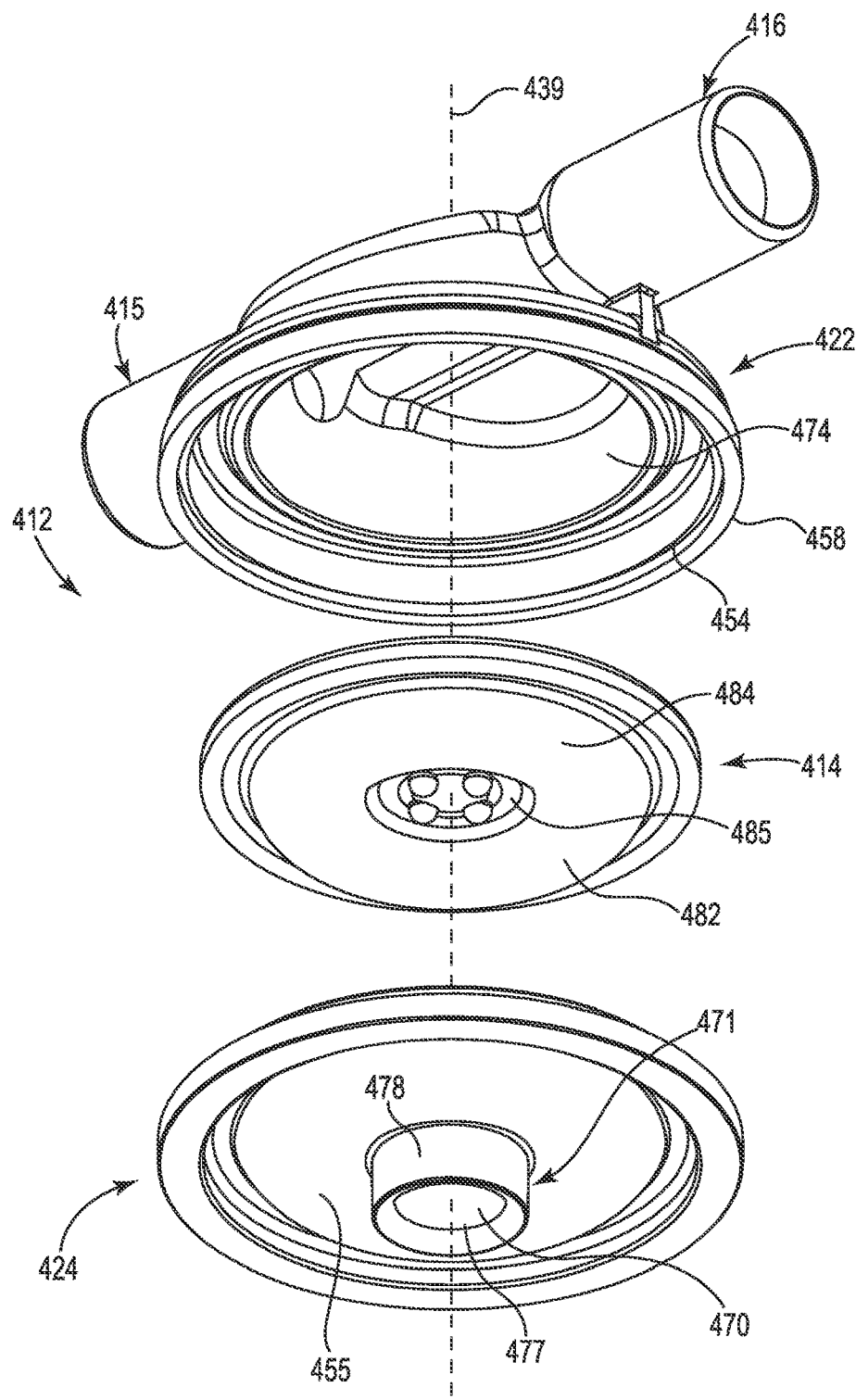
Figure 5C:
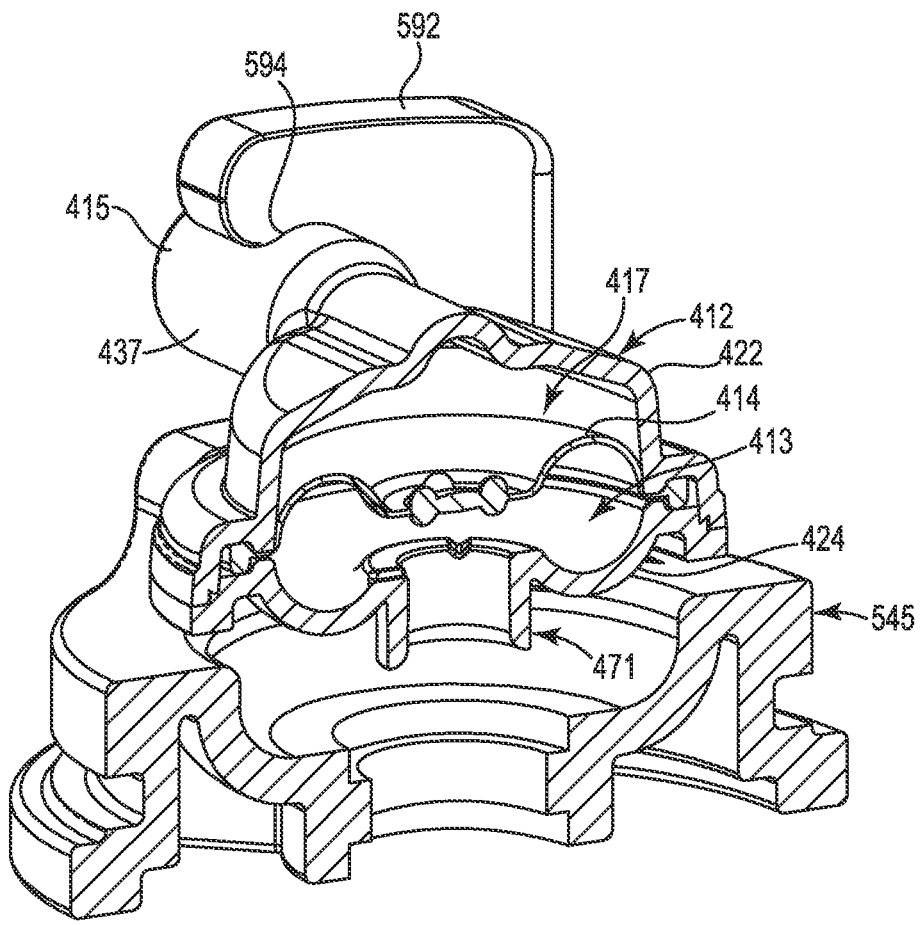

FIGS. 5A-5C show an exploded top perspective view, an exploded bottom perspective view, and an exploded side view of one embodiment of an exemplary pressure pod apparatus 412. The pressure pod apparatus 412 includes a pressure pod body 411 including at least a pod body portion 422 and a base body portion 424. For example, the pod body portion 422 which defines at least a portion of the liquid side cavity 417 (see, FIG. 5C) may include an annular clamping portion 454 extending from an annular edge 458 inward towards axis 439. A generally concave portion 453 (e.g., which includes an inner surface 474 adjacent the liquid side cavity 417) is located inward of the annular clamping region 454 relative to axis 439. The generally concave portion 453 or dome section terminating the annular clamping region 454 along axis 439 (e.g., a generally concave portion facing the base body portion 424 and lying along the axis 439 with its center on the axis 439) includes an inlet 415 and an outlet 416 extending from the pod body portion 422 (e.g., from the generally concave portion 453) to allow, for example, connection of tubing thereto, and to provide a path for liquid to enter and exit the liquid side cavity 417. For example, each of the inlet 415 and outlet 416 includes a cylindrical element 435 defining an inner surface 431 for mating with a tube. The cylindrical element 435 also includes an outer surface 437 configured for mating with connection apparatus (e.g., such as to mate with retention structure of a receptacle such as that shown in FIGS. 6A-6C).

The base body portion 424, for example, which defines at least a portion of the transducer side cavity 413, may include an annular clamping portion 456 extending from an annular edge 459 inward towards axis 439. A generally concave portion 455 (e.g., which includes an inner surface 475 adjacent the transducer cavity 413) is located inward of the annular clamping region 456 relative to axis 439. The generally concave portion 455 or dome section terminating the annular clamping region 456 along axis 439 (e.g., a generally concave portion facing the pod body portion 422 and lying along the axis 439 with its center on the axis 439) includes a cylindrical port 471 including an access opening 470 (e.g., defined through the generally concave portion 455) to allow, for example, fluid communication between the transducer side cavity 413 and a pressure transducer provided as part of the fluid processing system (e.g., as part of the control apparatus 360 shown in FIGS. 2-3). For example, the port 471 may include an inner surface 477 which may receive a portion of a connection apparatus (e.g., such as to mate with a receptacle such as that shown in FIGS. 6A-6C). Further, for example, the port 471 may include an outer surface 478 which may mate with a portion of a connection apparatus (e.g., such as to mate with a receptacle such as that shown in FIGS. 6A-6C). Further, the mating between the port 471 and the connection apparatus may provide a seal therebetween (e.g., such that transducer side cavity 413 is a fluid tight cavity (e.g., when taking into consideration the other pressure sensing components such as tubing, pumps, etc.). Such a seal may be provided in any suitable manner, such as with use of a sealing device (e.g., an o-ring, sealing material, etc.).

The pressure pod apparatus 412 further includes diaphragm 414. For example, the diaphragm 414 includes an annular clamp region 463 extending from an annular edge 462 inward towards axis 439. A deflection portion 461 (e.g., which includes a first surface 482 adjacent the transducer side cavity 413 and a second surface 481 adjacent the liquid side cavity 417) is located inward of the annular clamp region 463 relative to axis 439. The deflection portion 461 may include a bias such that it includes one or more regions which extend further in the transducer side cavity 413 than other regions thereof, or a bias such that it includes one or more regions which extend further into the liquid side cavity 417 than other regions, which may be referred to as a diaphragm bulge (e.g., an annular region 484 of the deflection portion 461 extends into the transducer side cavity further than a center region 485 at axis 439 as shown in FIG. 6, or for other configurations this may be reversed). Depending on whether the pressure to be measured is positive or negative, the diaphragm bulge may be placed in a particular direction giving a larger range in the pressure range of interest (e.g., either positive or negative). The annular clamp region 463, when the pressure pod apparatus 412 is assembled, is clamped between annular clamping region 456 of the base body portion 424 and the annular clamping region 454 of the pod body portion 422 to form the cavities 413 and 417 on either sides of the diaphragm 414. Any suitable processes and materials may be used to provide such an assembly (e.g., adhesives, thermal processing, etc.).

Figure 6A:
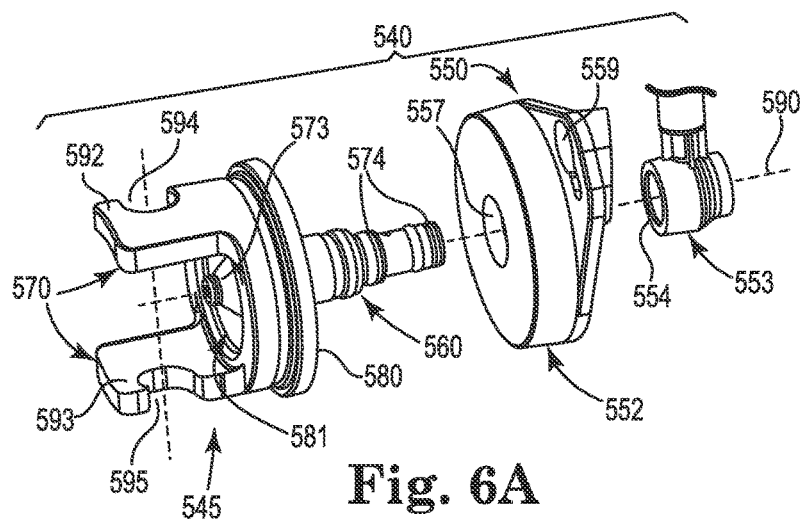
FIGS. 6A-6B show an exploded perspective view and a bottom view of a connection apparatus to connect a pressure pod apparatus, such as shown in FIGS. 5A-5C, to a fluid processing system (e.g., mount the pressure pod apparatus on a system housing).
Figure 6B:
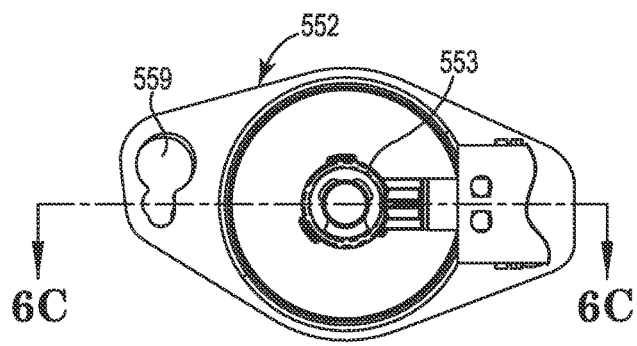
Figure 6C:
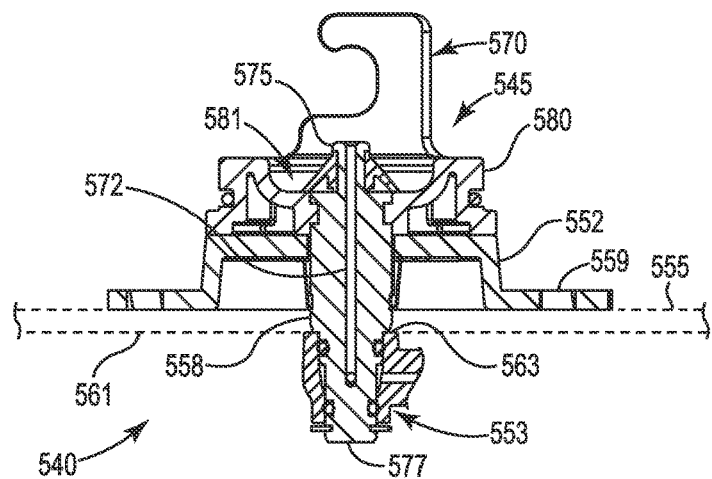
FIG. 6C is a cross-section of the connection apparatus shown in FIG. 6B taken at line 6C-6C.

FIGS. 6A-6B show an exploded perspective view and a bottom view of a connection apparatus 540 mountable on a system housing (e.g., such as system housing 11 shown in FIG. 1 or system housing 393 of FIGS. 2-3) to connect a pressure pod apparatus (e.g., provided as part of a disposable extracorporeal blood set), such as pod apparatus 412 shown in FIGS. 5A-5C, to a fluid processing system (e.g., such as fluid processing system 360 shown in FIGS. 2-3). FIG. 6C is a cross-section of the connection apparatus 540 shown in FIG. 6B taken at line C-C.

For example, the connection apparatus 540 may include a receptacle 545 configured to mate with a pressure pod apparatus (e.g., retain pressure pod apparatus 412 therein in a particular fixed position), and mounting apparatus 550 for mounting the mating receptacle 545 with respect to a system housing (see dashed system housing 555 in FIG. 6C). For example, mounting apparatus 550 may include an internal mounting structure 552 for receiving at least a portion of the mating receptacle 545 (e.g., port 560) in an opening 557 defined therein aligned with an opening defined in system housing 555. Further, the mounting apparatus 550 may include an internal connection structure 553 (e.g., tubing and tubing connectors, including, for example, a rotary coupler, tubes, etc.) that mate with a portion of the mating receptacle 545 (e.g., port 560) when inserted through the opening 557 of the internal mounting structure 552 to allow for fluid communication from inside of the system housing 555 to the transducer side cavity 417 of the pressure pod apparatus 412. The mounting of the mating receptacle 545 to the housing may be implemented with use of at least one of the internal mounting structure 552 being mounted to the system housing 555 (e.g., via one or more fasteners using openings 559), the internal connection structure 553, interference fit between a part of the mating receptacle 545 with the internal mounting structure 552 (e.g., an interference fit between a portion of the port 560 within the opening 557 defined in the internal mounting structure 552), or in any other suitable manner to provide a fixed mating receptacle 540 on the system housing 555 and/or relative thereto. Further, for example, an o-ring 558 or other suitable sealing device may be used to prevent liquid ingress into the interior of the system housing 555.

The mating receptacle 545 may include an annular body portion 580 extending along axis 590 defining a receiving region 581 to receiving a portion of the pressure pod apparatus 412 (e.g., to receive at least a part of the pod body portion 424 thereof). The port 560 (e.g., an elongate structure providing a fluid channel 572 therethrough) may extend along axis 590 through the annular body portion 580 from a first end region 575 to a second end region 577. The first end region 575 is configured for coupling with the port 471 of the pressure pod apparatus 412 (e.g., mate with the inner surface 477 thereof). For example, the mating between the port 471 and the first end region 575 of the port 560 may provide a seal therebetween (e.g., such that transducer side cavity 413 is a fluid tight cavity (e.g., when taking into consideration the other pressure sensing components such as tubing, pumps, etc.). For example, one or more lip seals 573 may be provided at the first end region 575 to sealingly mate with the inner surface 477 of the port 471 of the pressure pod apparatus 412. However, such seal to provide a fluid tight connection may be provided in any suitable manner, such as with use of any sealing apparatus on any of the components (e.g., an o-ring, sealing material, etc.).

The second end region 577 is configured for coupling with the internal connection apparatus 553 (e.g., mate with an inner surface 554). For example, the mating between the internal connection apparatus 553 and the second end region 577 of the port 560 may provide a seal therebetween (e.g., such that transducer side of the pressure sensor components provide fluid tight communication between the transducer side cavity 413 of the pressure pod apparatus 412 and a pressure transducer contained with the system housing 555. For example, one or more o-ring seals 574 may be provided at the second end region 577 to sealingly mate with the inner surface 554 of the internal connection apparatus 553. However, such a seal to provide the fluid tight connection may be provided in any suitable manner, such as with use of any sealing apparatus on any of the components (e.g., an o-ring, sealing material, etc.).

The mating receptacle 545 also may include retention structure 570 for coupling to and retaining one or more portions of the pressure pod apparatus 412 therein (e.g., maintaining the pressure pod apparatus in a stable fixed position). For example, as shown in FIGS. 6A and 6C, the retaining structure 570 may include U-shaped elements 592 and 593 positioned relative to and/or extending from the annular body portion 580 at a distance from axis 590. Such U-shaped elements 592-593 define channel openings 594-595 that are open in opposing directions and which lie along an axis 591 (e.g., an axis 591 that is orthogonal to axis 590). The channel openings 594-595 are configured to receive a portion of each of the inlet 415 and outlet 416 (e.g., which also lie along an axis), respectively (e.g., receive the outer surface 437 of each cylindrical element 435 configured for mating within the respective channel openings 594-595 of retention structure 570 (e.g., upon aligning the axis 439 of the pressure pod apparatus 412 with the axis 590 of the receptacle 545 and pushing and/or turning the pressure pod apparatus 412 about the axis 590 such that the outer surface 437 of each cylindrical element 435 is mated within the respective channel openings 594-595 of retention structure 570). However, any suitable mating configurations that provide for stable positioning of the pressure pod apparatus 412 on the system housing may be used and the present disclosure is not limited by only the mating configurations described herein.

With further reference to FIG. 1, which is illustrative of an extracorporeal fluid system such as shown and described with reference to FIGS. 2-3, each of the plurality of removable pressure pod apparatus 80A-80C (e.g., such as pressure pod apparatus 412 shown in FIGS. 5A-5C) which may be part of an extracorporeal blood set 22 are removably connectable to the system housing 11 (e.g., a system housing that contains one or more pressure transducers, a controller, valves, tubing, etc.) using connection apparatus 84A-84C (e.g., apparatus similar to that used to mount pressure pod apparatus 412 in mating receptacle 545 of connection apparatus 540 shown in FIGS. 5-6).

Also, as shown in FIG. 1, the system 10 further includes the pump apparatus 14 which may be used to automatically reposition the diaphragm (e.g., one of diaphragms 81A-81C) of a corresponding pressure pod apparatus 80A-80C towards the target (e.g., centered) measuring position. For example, such repositioning may be implemented using pump apparatus 14 in a controlled system (e.g., feedback system). For example, air may be infused or extracted using pump apparatus 14 (e.g., an air pump connected to the transducer side cavity of the pressure pod apparatus) through one or more valves 88A-88C (e.g., 2 port/2 way spring return solenoid valves) controlled by one or more corresponding switches S1-S3. As such, the pump apparatus 14 may sometimes be referred to herein as the automatic repositioning system (ARPS) air pump. In at least one embodiment, the air pump apparatus 14 may include a peristaltic pump which may be driven clockwise to infuse air into the system (e.g., in the air or transducer side cavity of a pressure pod) or may be driven counter-clockwise to remove air therefrom. For example, at least in one embodiment, each rotation of the peristaltic pump may deliver a known amount of air. As such, by monitoring the number of rotations of the pump, the amount of air delivered or removed by the pump apparatus 14 may be determined (e.g., this amount of air delivered may be adjusted taking into consideration atmospheric conditions).

Pump apparatus 14 may be connected in the system using any suitable configuration (e.g., a configuration formed of one or more pumps, valves, and tubes) to accomplish the functionality described herein. Further, pressure transducers (e.g., P1-P3, Ppump, etc.) may be any suitable transducers and may be operatively configured (e.g., a configuration in the form of valves and tubes) to accomplish the function of sensing pressures as desired for implementation of the functionality described herein.

As shown in the embodiment of FIG. 1, the controller 20 (e.g., within the system housing 11) is operatively coupled to receive one or more signals (e.g., representative of the pressures as sensed by pressure transducers, such as Ppump, P1-P3, etc.) and generate control signals for use in controlling pump apparatus 14. The pump apparatus 14 and valves 88A-88C via switches S1-S3 may be controlled to provide air to or remove air from the connection of the pump to the various components. For example, the controller 20 may be configured to operate a different valve (e.g., of valves 88A-88C) for each pressure pod apparatus 80A-80C to allow for repositioning of the diaphragm 81A-81C of each respective pressure pod apparatus 80A-80C. In other words, the plurality of valves 88A-88C allows a single pump apparatus to be used for repositioning the diaphragm of the multiple pressure pod apparatus 80A-80C. Further, for example, using the various pressure signals (e.g., including pressures associated with pressure pod apparatus 80A-80C and sensed using pressure transducers P1-P3, as well as pressures between pump apparatus 14 and valves 88A-88C sensed by pressure transducer Ppump), controller 20 may be used to reposition the diaphragm of each pressure pod apparatus 80A-80C such that valid pressure measurements may be obtained during treatment procedures.

The controller 20 may be any hardware/software architecture configured to provide the desired functionality. For example, the controller may include circuitry for sampling pressure measurements from the transducers, processing apparatus and associated software for processing data (e.g., signals representative of the pressures), output circuitry to generate control signals for use in diaphragm repositioning or presenting information on the graphical user interface (e.g., switch signals, air pump control or drive signals, etc.). As described herein with reference to FIGS. 2-3, for example, such controller functionality may be carried out by the apparatus 360 described therein.

Such processing apparatus, may be, for example, any fixed or mobile computer system (e.g., a personal computer or mini-computer associated with, for example, a fluid treatment or processing system, such as a dialysis system). The exact configuration of the computing apparatus is not limiting and essentially any device capable of providing suitable computing capabilities and control capabilities (e.g., perform diaphragm repositioning, provide a graphical user interface, for example, to provide instructions to a user, perform treatments, etc.) may be used. Further, various peripheral devices, such as a computer display, mouse, keyboard, memory, printer, scanner, are contemplated to be used in combination with processing apparatus, and its associated data storage. For example, data storage may allow for access to processing programs or routines and one or more other types of data that may be employed to carry out the illustrative methods and functionality as described herein.

In one or more embodiments, the methods or systems described herein may be implemented using one or more computer programs or processes (or systems including such processes or programs) executed on programmable computers, such as computers that include, for example, processing capabilities, data storage (e.g., volatile or non-volatile memory and/or storage elements), input devices, and output devices. For example, the systems and methods described herein may be considered to include multiple processes or programs that may be implemented alone or in combination. Program code and/or logic described herein may be applied to input data to perform functionality described herein and generate desired output information. The output information may be applied as input to one or more other devices and/or processes as described herein or as would be applied in a known fashion. For example, processing programs or routines may include programs or routines for performing various algorithms, including standardization algorithms, comparison algorithms, or any other processing required to implement one or more embodiments described herein, such as those for performing averaging of measurement data, filtering of sensed signals, generation of control signals, etc.

Software or programs used to implement the functionality described herein may be provided using any programmable language, e.g., a high level procedural and/or object orientated programming language that is suitable for communicating with a processing apparatus. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the methods and systems described herein may be implemented using a computer readable storage medium, configured with a computer program, where the storage medium so configured causes the processing apparatus to operate in a predefined manner to perform functions described herein.

Further, as shown in FIG. 1, an air filter 16 may be provided and connected between the air pump apparatus 14 and the one or more ports associated with the various components (e.g., pressure pod apparatus 80A-80C). Such an air filter may be a clarifier air filter when connecting sterile components to such ports. In other words, the clarifying air filter provides clarifying air to maintain the sterile components connected at such ports.

Figure 7:
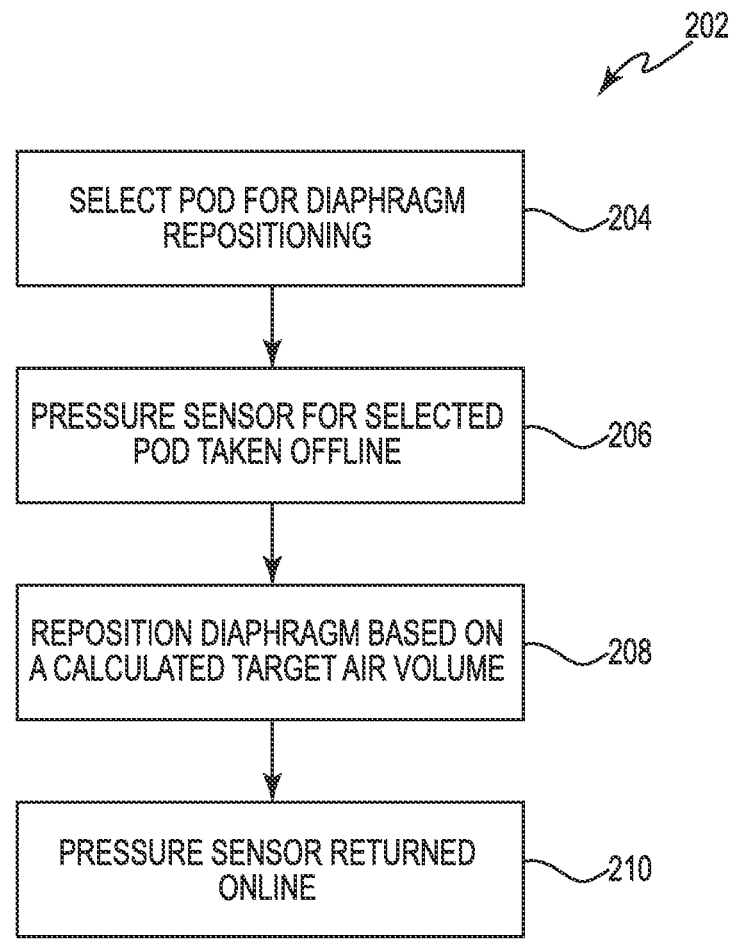
FIG. 7 shows a flow diagram of an exemplary diaphragm repositioning method for a pressure measurement apparatus (e.g., including a pressure pod apparatus of an extracorporeal blood set connected to a system housing of a system, for example, such as shown generally in FIGS. 1-3).
Figure 8:
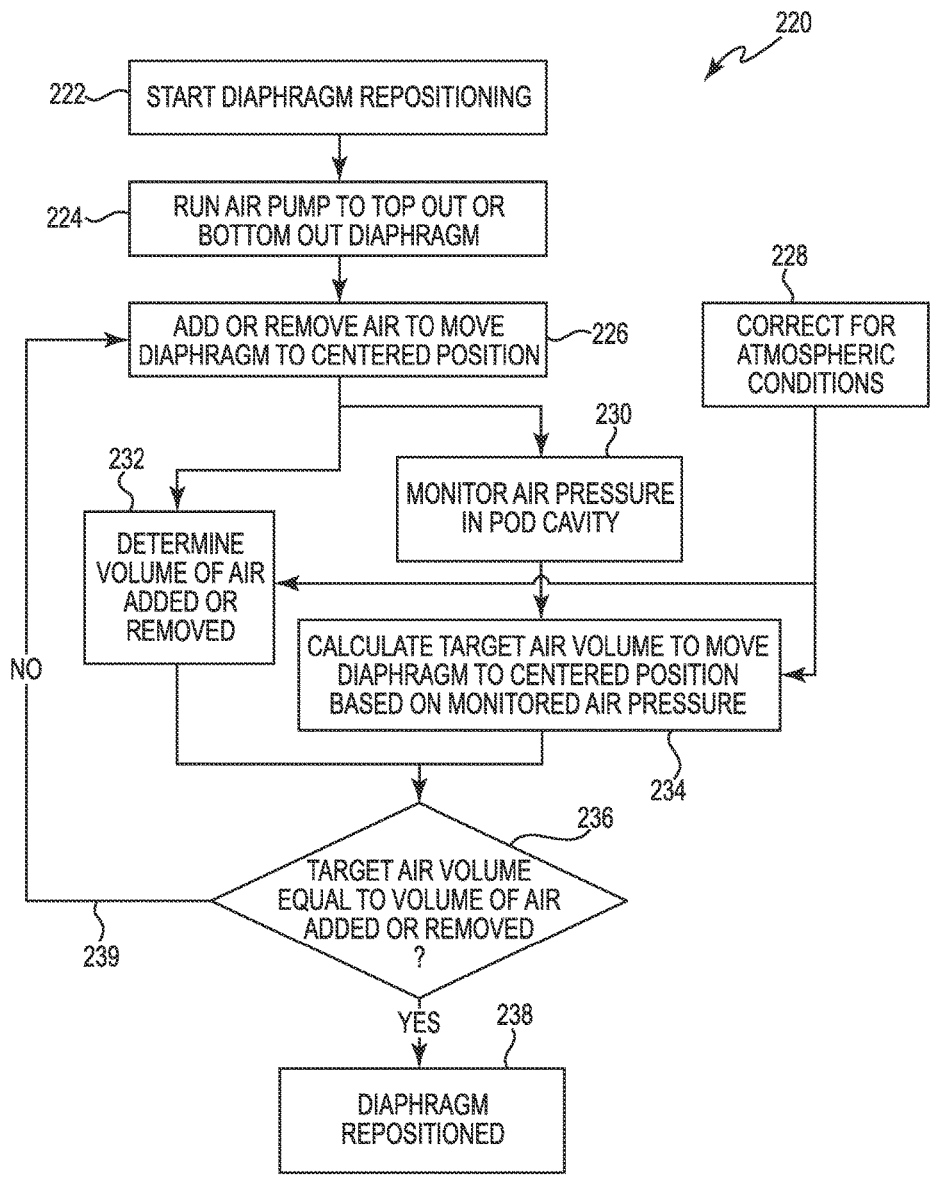
FIG. 8 shows a flow diagram of a more detailed exemplary diaphragm repositioning method.
Figure 9:
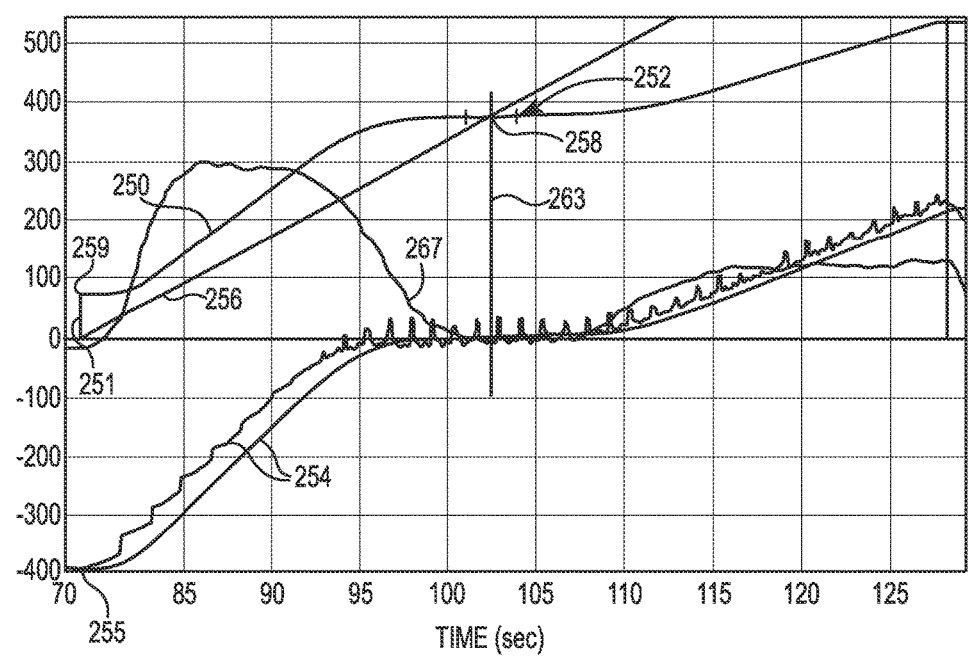
FIG. 9 is a graph for use in describing exemplary diaphragm repositioning systems and methods.

With reference to FIGS. 7-9, one or more embodiments of diaphragm repositioning processes shall be described that may be implemented using systems and components, for example, such as those shown and described with reference FIGS. 1-6. The methods or processes shall primarily be described with reference to the elements of FIG. 1, however, it will be apparent that any fluid handling systems may be used to implement such methods.

For example, the flow diagram of FIG. 7 shows an exemplary repositioning method 202 for repositioning the diaphragms of each of the plurality of pressure measurement apparatus to a target measuring position (e.g., repositioning each diaphragm 81A-81C of a plurality of pressure pod apparatus 80A-80C of an extracorporeal blood set 22 connected to a housing 11 of an extracorporeal blood treatment system 10 in a fixed or non-fixed state). For example, the system housing 11 contains one or more pressure transducers (e.g., P1-P3 and Ppump) and an air pump apparatus 14 (e.g., an automatic repositioning air pump). Further, the one or more connection elements 13, including, for example, one or more ports of mating receptacles 84A-84C, one or more tubes, one or more valves, or any other elements, operatively connect the pump apparatus 14 to the pressure pod apparatus 80A-80C of the extracorporeal blood set 22 (e.g., the transducer side cavity thereof), as well as operatively connect the one or more pressure transducers (e.g., P1-P3 and Ppump) to the pressure pod apparatus 80A-80C of the extracorporeal blood set 22 (e.g., the transducer side cavity thereof).

The diaphragm repositioning method 202 may include selecting one of the pressure pod apparatus 80A-80C for diaphragm repositioning (block 204). Upon selection, the pressure transducer corresponding to the selected pressure pod apparatus is taken off-line (block 206). Such diaphragm repositioning may be performed during priming of a treatment system, or may be, for example, performed periodically (e.g., a self-test every couple hours or so) during treatment. For example, in at least one embodiment, each pressure pod apparatus 80A-80C is operatively connected to a corresponding pressure transducer P1-P3 which during therapy or treatment is operable to provide pressure measurements representative of the fluid flow in fluid side cavity (e.g., separated from the transducer side cavity 85A-85C by diaphragm 81A-81C) of the corresponding pressure pod apparatus 80A-80C (e.g., by the measurement of pressure in the transducer side cavity). The system 10 uses such air pressure measurements from the corresponding pressure transducer for therapy pressure monitoring (e.g., such therapy pressure monitoring used for control of a therapy being delivered).

So that valid pressure measurements are provided during, for example, treatment of a patient, the diaphragm 81A-81C of each pressure pod apparatus 80A-80C is repositioned as described herein. However, when the diaphragm of a particular pressure pod apparatus is selected for repositioning, the use of air pressure measurements for therapy pressure monitoring from the pressure transducer corresponding to the pressure pod apparatus having its diaphragm repositioned are temporarily discontinued. In other words, pressure measurements associated with the selected pressure pod apparatus are not used for a particular period of time for control of therapy so that the diaphragm of the selected pressure pod apparatus may be repositioned. As such, the pressure transducer associated with the selected pressure pod apparatus is taken off-line and is not used for therapy pressure monitoring. For example, if pressure pod apparatus 80A is selected for diaphragm repositioning, then the pressure transducer P1 is taken off-line, but pressure measurements made using P2-P3 using the other pressure pod apparatus 80B-80C continue to be used for therapy monitoring purposes.

After the selected pressure pod apparatus is taken off-line (block 206), then the diaphragm thereof is repositioned to a target measuring position based on a calculated target air volume (block 208). For example, as described in further detail with reference to FIG. 8, generally, the air pump apparatus 14 is controlled to bottom out the diaphragm 81A on the base body portion of the selected pressure pod apparatus 80A by removing air from the transducer side cavity 85A thereof, or the air pump apparatus 14 is controlled to top out the diaphragm 81A on the pod body portion by adding air to the transducer side cavity 85A of the pressure pod apparatus 80A. Thereafter, and as the air pressure in the transducer side cavity is monitored by pressure transducer P1, the air pump apparatus 14 is controlled to add air to the transducer side cavity 85A after the diaphragm 81A is bottomed out to move the diaphragm 81A toward a target measuring position based on the calculated target air volume, or the air pump apparatus 14 is controlled to remove air from the transducer side cavity 85A after the diaphragm 81A is topped out to move the diaphragm 81A toward a target measuring position based on the calculated target air volume. As further described herein, the calculated target air volume is representative of the air volume necessary or required to move the diaphragm 81A to the target measuring position based at least on the monitored air pressure by pressure transducer P1. As air is added to or removed from the transducer side cavity, the target air volume necessary to move the diaphragm 81A to the target measuring position is iteratively calculated (e.g., due to the fact that the transducer side cavity pressure monitored by transducer P1 is changing as air is added due to various factors, such as tube compliance) until it is determined that the diaphragm 81 is repositioned in the target measuring position based on a comparison of the calculated target air volume and a total amount of air added to or removed from the transducer side cavity by the air pump apparatus 14 (e.g., determined based, for example, on the monitoring of pump rotations).

After the diaphragm 81A of the selected pressure pod apparatus 80A has been repositioned (block 208), then the pressure transducer P1 is returned on-line. In other words, the pressure measurements made thereby may again be used for treatment purposes. Thereafter, the diaphragm of another pressure pod apparatus, such as diaphragm 81B of pressure pod apparatus 80B, may be selected for diaphragm repositioning and pressure transducer P2 which is used to provide pressure measurements for treatment purposes is taken off-line. Selection of pressure pod apparatus 80A-80C and repositioning of the diaphragms 81A-81C thereof may be performed in any desired sequence. At least in one embodiment, repositioning of the diaphragm of each of the pressure pod apparatus 80A-80C is performed sequentially and repeated as needed, for example, during delivery of treatment. For example, the system 10 may include a plurality of valves 88A-88C each corresponding to one of the pressure pod apparatus 80A-80C. The controller 20 may be configured to operate a different valve for each of the pressure pod apparatus 80A-80C to allow the diaphragm of each of the pressure pod apparatus 80A-80C to be separately repositioned during different time periods (e.g., as treatment is delivered).

FIG. 8 shows a more detailed flow diagram of an exemplary diaphragm repositioning method 220 for use in repositioning the diaphragm of one or more pressure pod apparatus. FIG. 8 shall be described with reference to only the repositioning of the diaphragm 81A of pressure pod apparatus 80A for simplicity as the other diaphragms may be repositioned in a like manner. Further, reference shall be made to FIG. 9 which provides a graphical representation of the diaphragm repositioning process. FIG. 9, for example, shows graph lines 254 representative of an unfiltered and filtered measured pressure; a graph line 250 representative of a calculated target air volume; and a graph line 256 representative of a total volume of air added (e.g., using the pump apparatus). Yet further, although it is described herein that the diaphragm repositioning process may be carried out by first topping out the diaphragm in the pressure pod apparatus and then removing air to move the diaphragm to a target measuring position, for simplicity, the description with reference to FIGS. 8-9 shall be with reference only to diaphragm repositioning carried out by first bottoming out the diaphragm and then adding air to move the diaphragm to the target measuring position.

As shown in FIGS. 8-9, the diaphragm repositioning process 220 is started upon selection of the pressure pod apparatus 80A for which the diaphragm 81A thereof is to be repositioned (e.g., the pressure transducer P1 being taken off-line and not used for treatment monitoring during the repositioning process as described with reference to FIG. 7) (block 222). Further, for example, with reference to FIG. 1, the valve 88A corresponding to pressure pod apparatus 80A is open while the valves 88B-88C associated with the other pressure pod apparatus 88B-88C are closed. The air pump apparatus 14 is controlled to remove air from the transducer side cavity 85A of the pressure pod apparatus 80A so as to bottom out the diaphragm 81A on the base body portion thereof (e.g., base body portion 424) (block 224). As shown in FIG. 9, for example, air is removed until a negative pressure 255 as measured, for example, by pressure transducer P1 and/or Ppump, necessary to bottom out the diaphragm 81A is attained (e.g., −400 mmHg).

The pump apparatus 14 is then controlled to add air to move the diaphragm 81A to the target measuring position (block 226). For example, at least in one embodiment, an initial calculated target air volume after bottoming out the diaphragm 81A is represented by point 259 on graph line 251 in FIG. 9. This initial calculated target volume may represent the added volume of air that would be required to move the diaphragm from the bottomed out position to the centered or measuring position if the pressure on the fluid side of the diaphragm was actually equal to the measured pressure on the transducer side of the diaphragm (e.g., as measured by pressure transducer P1 and/or Ppump). However, at least in one exemplary embodiment, since pressure on the transducer side of the diaphragm is initially more negative than the pressure on the fluid side of the diaphragm when the diaphragm is bottomed out, the initial calculated target air volume 259 will be greater than the initial pump delivered air volume (which is initially zero) resulting in the generation of commands to the controller 20 to add air to the transducer side cavity 85A.

As air is added to move the diaphragm 81A to the target measuring position, the air pressure at the transducer side cavity 85A is monitored (block 230) and a target air volume required to move the diaphragm to the target measuring position is calculated (block 234). As shown in FIG. 9, as the measured pressure 254 increases, the calculated target air volume required to move the diaphragm 81A to the target measuring position changes (e.g., also increases; not linearly). As described further herein, the calculated target air volume may be adjusted or corrected for atmospheric conditions (block 228) (e.g., may be adjusted using a user input value representative of atmospheric pressure at a particular location, may be adjusted using a value representative of atmospheric pressure measured by an atmospheric pressure sensor of the system, etc.).

Further, as described herein, the calculated target air volume required to move the diaphragm to the target measuring position (block 234) may be based on one or more other parameters in addition to the pressure measurements (e.g., pressure measurements from P1), including, for example, an actual volume defined within the transducer side cavity 85A (e.g., when the diaphragm 81A is in the target measuring position) and an actual volume defined by one or more connection elements 13 used to couple the air pump apparatus 14 and pressure transducer P1 to the transducer side cavity 85A (e.g., connection elements including receptacles, tubes, filter housings, pressure sensors, shafts, valves, manifolds, rotary couplings, etc., as well as the compliance of one or more of such elements). In other words, in one or more embodiments, the defined volume contributed by the connection elements 13 located in the path between the pump apparatus 14 and the transducer side cavity 85A are used in determining the calculated target air volume, along with the defined volume (e.g., measured or determined volume) of the transducer side cavity 85A when the diaphragm 81A is considered to be in the target measuring position.

The total volume of air added is also determined (block 232). Any suitable process of measuring the volume of air added into the path between the pump apparatus 14 and the pressure pod apparatus 80A may be used. The amount of air added is generally represented by graph line 256 in FIG. 9. As shown therein, the total volume of air added 256 is generally a linear function, although the air may be added at any rate, whether the same or different over time. In at least one embodiment, a pump apparatus (e.g., a peristaltic pump) is used to provide air and/or remove air. Such a pump apparatus may deliver a known amount of air per rotation. As such, the total amount of air added may be determined by monitoring the rotation of the pump apparatus over time. The total amount of air added may be adjusted or corrected for atmospheric conditions (block 228) (e.g., may be adjusted using a user input value representative of atmospheric pressure at a particular location, may be adjusted using a value representative of atmospheric pressure measured by an atmospheric pressure sensor of the system, etc.). Further, for example, in line flow sensors (e.g., such as Honeywell AMW 40000 Series sensors, etc.) may also be used to determine the total amount of air added to the system. Such in line sensors when used to measure the air flow (typically in SCCM—standard cubic centimeters per minute) which may simplify calculations as such sensors may correct the air flow to standard atmosphere and temperature.

As shown in FIG. 8, the calculated target air volume (block 234) is compared to the total volume of air added (block 232) to determine whether the diaphragm 81A is repositioned to the target measuring position (block 236). For example, at least in one embodiment, if the total air volume added is equal to the calculated target air volume (e.g., within a predetermined tolerance) then the diaphragm 81A has been repositioned to the target measuring position (block 238) and, for example, another pressure pod apparatus may be selected for diaphragm repositioning. However, if such is not the case, then air is continued to be added by the air pump apparatus 14 under control of controller 20 (block 226) and the process is reiterated as represented generally by line 239. In one or more embodiments, air may be removed if the total volume of air added is greater than the target calculated volume (e.g., under commands generated by the closed loop system where the pump command is proportional to calculated target volume minus the total volume added). For example, such may occur if the change in pressure causes a short term heating or cooling that subsequently decays to ambient or if the tubing slowly expands or contracts in response to the pressure changes.

Such an iterative process is illustrated in FIG. 9. For example, the pressure measurements shown by graph line 254 taken over time are used in the calculation of the target air volume shown by graph line 250. Intersection 258 shows an exemplary time when the calculated target air volume 250 is determined to be equal to the total volume of air added 256. For example, at this point in time, the diaphragm 81A may be indicated as being repositioned to the target measuring position. It will be recognized that the target measuring position may be a range such that, for example, when the total volume of air determined to have been added to the system (block 232) is within a certain range 252 (represented generally in FIG. 9) of the calculated target air volume 250, then diaphragm 81A may be indicated as being repositioned. Further, for example, in one or more embodiments, it may be desired for the determined volume of air added (block 232) to meet and/or exceed the calculated target air volume 250 over a number of samples prior to determining that the diaphragm 81A has been repositioned. In other words, the target measuring position may refer to a particular position or may refer to a target measuring range of adequate diaphragm positions suitable for providing valid pressure measurements for treatment monitoring. Although the graph lines shown in FIG. 9 show that, for example, target volume is continued to be calculated, pressure sensor readings are continued to be measured, and total air added continues to be determined after time 263 (e.g., representative of the time the diaphragm has been determined to have been repositioned to the target measuring position and the repositioning process completed), such is generally not the case and the extensions of such graph lines after time 263 are provided for illustration only to show the nature of such graph lines as if the repositioning process for diaphragm had not been completed at time 263.

In one or more embodiments, the target air volume required to move the diaphragm 81A to the target measuring position is calculated using the pressure measured by, for example, pressure transducer P1 and/or Ppump, taking into consideration the defined volume between the air pump apparatus 14 (e.g., the position at which the air is introduced) and the diaphragm 81A when at its desired target measuring position (e.g., including, for example, one half of the volume of the pressure pod apparatus or, for example, a certain percentage of the total volume defined by the pressure pod representative of the volume of air in the transducer side cavity when the diaphragm is at its desired target position, as well as a defined volume of all the other connection elements located between the pump apparatus 14 and the pod apparatus 80A connected to the receptacle on the system housing 11). One will recognize, that the one or more connection elements located between the pump apparatus 14 and the connected pressure pod apparatus may differ depending upon the system and/or implementation thereof. As such, although one or more various specific configurations are described herein, the calculations necessary for determining target air volume for any particular configuration will be similar, but likely different than those for the specific configurations described herein. For example, certain configurations may or may not include one or more of the various connection elements located between the pump apparatus and the connected pressure pod apparatus, certain configurations may have a target measuring position that is not necessarily at the exact center of the pressure pod apparatus, the compliance of the various tubes used for connection between the pump apparatus 14 and the connected pressure apparatus may differ, etc.

One exemplary set of equations for calculation of the target air volume required to move the diaphragm 81A to the target measuring position may include the following:

Let the following definitions apply:

$P_{atmos}$=Current atmospheric pressure (mmHg) (e.g., 760 mmHg, a user inputted pressure provided, for example, during set up, an atmospheric pressure sensed by an atmospheric pressure sensor of the treatment system, etc.);

$P_{arpsX}$=Sensed ARPS pressure (mmHg) (e.g., pressure sensed by P1 or Ppump representative of the pressure in the transducer side cavity);

$P_{arpsXa}$=Absolute ARPS pressure (mmHg)=$P_{arpsX}$+$P_{atmos}$;

Ctube=Compliance of tube and/or one or more other connection elements (e.g., determined by tests, input by user, or provided in any other manner), for example, the compliance of the tubing and any other connection elements (excluding the pressure pod itself) may be determined by running the ARPS pressure from negative (−) 400 mmHg to positive (+) 400 mmHg with the pressure pod apparatus removed and either the orifice that normally interfaces with the pressure pod apparatus blocked (but with the valve associated with the pressure pod apparatus open to allow air from the pump to reach the blocked orifice) or simply with the valve associated with the pressure pod apparatus closed to block air provided by the pump from reaching the pod (e.g., the VHalfPod volumes being different for the different cases); for increasing pressures (which will always be the case when starting from a bottomed out diaphragm position) then, the slope which represents the compliance may be determined (e.g., in one case and configuration, the compliance was determined to be 5.72 microliters air @ 1 atmos/ (mmHg sensed pressure change); further, this compliance value may be recalibrated by service technicians on a service schedule to determine and calibrate for a change in compliance in a manner similar to that described above to determine the compliance;

PbotX=Sensed ARPS pressure when diaphragm of pod apparatus is bottomed out (mmHg) (e.g., pressure sensed by P1 or Ppump, may be about negative 400 mmHg); and PbotXa=Absolute ARPS pressure when diaphragm of pod apparatus is bottomed out (mmHg) (e.g., pressure sensed by P1 or Ppump, may be about 760 mmHg minus 400 mmHg which is equal to about 360 mmHg).

Taking into consideration the compliance of one or more connection elements connecting the pump apparatus 14 to the pressure pod apparatus as well as the defined volumes of such components (including defined volumes (micro-liters) of, for example, connection elements associated with the path of the air from the air pump apparatus 14 to the transducer side cavity 85A of the pressure pod apparatus 80A, such as a shaft associated with the pressure transducer P1, a rotary coupler associated with connection of the tubing to the mating receptacle, one or more filter housings, one or more tubes, one or more pressure transducers (e.g., P1, Ppump,), etc.), at any given ARPS Pressure then:

VTubeX=Volume of air (at 1 atmos) required to be added, taking into consideration the compliance of the connection elements, to bring the connection elements from the bottomed out pressure to the current ARPS pressure or, in other words, VTubeX=(ParpsXa−PbotXa)*Ctube;

VHalfPod=Desired pod volume to center diaphragm (microliters) (e.g., will depend on what is selected as the centered or target measuring position in the pod apparatus; may be, for example, 1500 microliters), and also the point where the air path is blocked when determining Ctube);

VHalfPodX=ARPS (1 atmos) air needed to provide desired pod volume (at current ARPS pressure) to center diaphragm (microliters);

$$VHalfPodX = VHalfPod*(ParpsX + Patmos)/Patmos$$
$$= VHalfPod*ParpsXa/Patmos;$$

Then, VTarget=ARPS (1 atmos) target air volume needed to bring the connection elements from the bottomed out pressure to the current ARPS pressure and to provide a desired pod volume (at current ARPS pressure) in order to center the diaphragm may be written as:

$$Vtarget=VTubeX+VHalfPodX.$$

The calculated target air volume (Vtarget) required to move the diaphragm to the target measuring position may be calculated in at least this exemplary manner. However, it will be recognized that other ways of calculating the target volume based on the pressure sensed in the transducer side cavity may also be used. For example, the target air volumes for different portions of the path between the air pump apparatus 14 and the transducer side cavity of the pressure pod apparatus may be separated in a different manner for the calculation. For example, instead of summing the calculated target air volume for the transducer side cavity and the calculated target air volume for the other connection elements to provide a calculated target air volume needed to repositioned the diaphragm to the target measuring position, one could sum the calculated target air volumes for different portions of the path (e.g., sum the calculated target air volume from the valve including the pressure transducer P1 and the transducer side cavity of the pressure pod apparatus with the calculated target air volume from the air pump to the valve including the pressure transducer Ppump, sum the calculated target air volumes of a path separated into more than two parts, etc.). Further, as will be recognized, the equations presented herein for calculating target air volume take into consideration the atmospheric conditions (e.g., elevated atmospheric pressure) and as such adjust for such conditions.

One embodiment of an exemplary target volume based diaphragm repositioning algorithm operating such as described generally with reference to FIGS. 8-9 may provide an automated sequence to center the diaphragm of each pressure pod without relying on a pressure derivative calculation, such as described in the Background herein. The algorithm may use the automatic repositioning system (ARPS) air pump to first remove air from the pressure pod air cavity and bottom out the pressure pod diaphragm by pulling the air cavity pressure to a more negative value than any operating pressure expected for that pod. The ARPS pump may then be commanded to add air into the pressure pod air cavity and the resulting pressure may be monitored to calculate the total volume of air to be added from the bottomed out position that will result in the diaphragm being centered in the pod apparatus (which may be referred to as the "target volume"). The actual volume of air added by the APRS air pump may be determined by monitoring the rotation of the ARPS air pump which delivers a known amount of air for each rotation. When the actual amount of ARPS air delivered matches the calculated "target volume," then the diaphragm is centered and pressure readings from the pod pressure sensor correspond to the fluid pressure on the fluid side of the diaphragm. The air volume calculations may be corrected for ambient atmospheric pressure effects. For example, the atmospheric pressure value may come from either an atmospheric pressure sensor in the device itself or a fixed value may be entered by a service technician when the device is set up at a specific location. Electronically controlled valves may control which pod(s) is connected to the ARPS pump air output line so that the repositioning technique can be applied sequentially to each pressure pod.

Since this repositioning method does not rely on a calculated pressure derivative, it is less sensitive to pressure sensor noise and peristaltic pump pressure peaks. Optionally, the pressure derivative (shown graphically as line 267 in FIG. 9) may be monitored as an independent verification of correct diaphragm repositioning by the target volume based repositioning algorithm (e.g., note in FIG. 9 that the pressure derivative goes to zero in the time region when the calculated target air volume 250 intersects with total amount of air added graph line 256 confirming the repositioning of the diaphragm to the target measuring position).

The algorithm described may start the repositioning from a bottomed out pod diaphragm position. However, as described herein, for pressure pods that normally operate in positive pressures, it may be more time optimal to start from a topped out diaphragm position, and then remove air until the target volume is reached. The same target volume techniques described herein can be applied in such a case.

One specific algorithm implementation, which starts from a bottomed out diaphragm position, is provided below. The specific algorithm implementation samples pressure readings at 10 Hz (0.1 second time intervals) and executes the following steps. The steps below are a summary of the algorithm:

Step 1—Set or select a pod apparatus 80A to be repositioned (e.g., select Access Pressure Pod);

Step 2—Run ARPS pump 14 to equalize pressure with selected pod apparatus 80A being repositioned while all valves (88A-88C) corresponding to the pressure pods (80A-80C) remain closed (no air connection of the pressure pods (80A-80C) to the ARPS pump 14);

Step 3—Open pod valve 88A for the selected pod apparatus 80A to be repositioned to connect ARPS pump 14 to the pod transducer side air cavity 85A and verify match within 20 mmHg between ARPS pressure sensor (Ppump) and pressure sensor P1 corresponding to the selected pressure pod 80A. Continue monitoring for pressure match during the following repositioning steps until valve 88A connecting the ARPS pump 14 to the selected pressure pod 80A is closed. If pressures mismatch by more than 20 mmHg for 5 seconds or longer, set fault indicator and stop repositioning on this pressure pod.

Step 4—Run APRS pump 14 to remove air until pressure is at least 50 mmHg less than the lowest expected operating pressure for that pod (e.g., if lowest expected operating pressure is −400 mmHg, then run ARPS pump until pressure reaches −450 mmHg). This will bottom out the pod diaphragm 81A.

Step 5—Run ARPS pump 14 to start adding air to pod transducer side air cavity 85A and calculate target volume required to move the diaphragm 81A to the target measuring position at each algorithm iteration based on ARPS pressure sensor reading (P1 or Ppump) and suitable equations (see equations described herein with reference to FIGS. 8-9). Also, at each algorithm iteration step, calculate the volume of air added by the ARPS pump after the diaphragm was bottomed out (total volume added). A low pass filter (3 rad/s corner frequency may be applied for this implementation, value dependent on application dynamics) to the calculated ARPS air volume added.

Step 6—Continue running ARPS pump 14 to add air to pod transducer side air cavity 85A until the filtered ARPS air volume (total air volume added) exceeds the calculated target volume for at least 4 iteration samples. Alternately, for example, the ARPS pump flow rate command may be based on the difference between the calculated target volume and the total volume of air added by the ARPS pump since step 5 starts the adding of air to the pod transducer side air cavity (e.g., which may be referred to as closed loop control of added air volume). If the pressure reaches the maximum allowed pressure for the pod (e.g., 400 mmHg) before the total volume added reaches the calculated target volume, then set a fault indicator and terminate the repositioning for the selected pod apparatus.

Step 7—Stop the APRS pump 14 and wait for a short time to allow pressures and filters to stabilize (e.g. 3 seconds)

Step 8—Run the ARPS pump 14 for a short time (e.g., 1 second) to remove air from the air cavity to compensate for filter delays on the sensed pressures and calculated ARPS volume. Alternately, if closed loop control of added air volume is used (see step 6), this step may not be necessary. Diaphragm repositioning for the selected pressure pod apparatus is complete.

Step 9—Close the valve 88A connecting the ARPS pump 14 to the selected pod 80A.

Step 10—Repeat steps 2-8 for a next pressure pod 80B (e.g., a Filter pod).

Step 11—Close the valve 88B connecting the ARPS pump 14 to the next pressure pod 80B (e.g., the Filter pod).

Step 12—Repeat steps 2-8 for still another pressure pod 80C (e.g., an Effluent pod).

Step 13—Close the valve 88C connecting the ARPS pump 14 to the pod 80C (e.g., the Effluent pod).

Further, for example, if diaphragm repositioning is not completed within a timeout period for a pressure pod apparatus (e.g., 180 seconds), the algorithm may set a "FaultReposition" flag and terminate. Further, for example, although the specific algorithm implementation presented uses 10 Hz pressure samples, the algorithm may be implemented at other sample rates as dictated by alternate system architectures and pressure dynamics (e.g., 60 Hz pressure data and target data updates may be used).

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An extracorporeal blood treatment system comprising:
a pressure measurement apparatus comprising:
  at least a pod body portion and a base body portion; and
  a diaphragm separating a fluid side cavity defined at least in part by the pod body portion from a transducer side cavity defined at least in part by the base body portion, wherein the fluid side cavity is in fluid communication with an inlet and an outlet, and further wherein the diaphragm is displaceable from a target measuring position into the fluid side cavity towards the pod body portion and is displaceable from the target measuring position into the transducer side cavity towards the base body portion;
an air pump apparatus coupled to the transducer side cavity via one or more connection elements to add air to or remove air from the transducer side cavity;
at least one pressure transducer operatively coupled to the transducer side cavity to sense air pressure therein;
a controller operatively coupled to the air pump apparatus and the at least one pressure transducer to reposition the diaphragm to the target measuring position, wherein the controller is configured to:

control the air pump apparatus to bottom out the diaphragm on the base body portion by removing air from the transducer side cavity and/or to top out the diaphragm on the pod body portion by adding air to the transducer side cavity;

monitor the air pressure in the transducer side cavity sensed by the at least one pressure transducer;

calculate a target air volume required to move the diaphragm to the target measuring position based at least on the monitored air pressure; and control the air pump apparatus to add air to the transducer side cavity after the diaphragm is bottomed out to move the diaphragm toward a target measuring position based on the calculated target air volume or to remove air from the transducer side cavity after the diaphragm is topped out to move the diaphragm toward a target measuring position based on the calculated target air volume, wherein, as air is added to or removed from the transducer side cavity, the controller is configured to iteratively calculate the target air volume required to move the diaphragm to the target measuring position based at least on the monitored air pressure until the controller determines that the diaphragm is in the target measuring position.

2. The system of claim 1, wherein the controller is configured to iteratively calculate the target air volume until the controller determines that the diaphragm is in the target measuring position based on a comparison of the calculated target air volume and a total amount of air added to or removed by the air pump apparatus.

3. The system of claim 2, wherein the controller is further configured to determine the total amount of air added or removed by monitoring rotation of the air pump apparatus which delivers or removes a known amount of air per rotation.

4. The system of claim 2, wherein the controller is configured to determine that the diaphragm is in the target measuring position when the amount of air added to or removed from the transducer side cavity meets the calculated target air volume.

5. The system of claim 1, wherein the calculation of target air volume is adjusted for atmospheric conditions.

6. The system of claim 5, wherein the calculation of target air volume is adjusted using a user input value representative of atmospheric pressure at a particular location.

7. The system of claim 5, wherein the calculation of target air volume is adjusted using a value representative of atmospheric pressure measured by an atmospheric pressure sensor of the system.

8. The system of claim 1, wherein the controller is configured to calculate the target air volume required to move the diaphragm to the target measuring position based at least on the monitored air pressure, an actual volume defined by the transducer side cavity desired to move the diaphragm to the target measuring position, and an actual volume defined by the one or more connection elements used to couple the air pump apparatus to the transducer side cavity of the pressure measurement apparatus.

9. The system of claim 8, wherein the one or more connection elements used to couple the air pump apparatus to the transducer side cavity comprise one or more tubes, and further wherein the controller is configured to calculate the target air volume required to move the diaphragm to the target measuring position based at least on the monitored air pressure, the actual volume defined by the transducer side cavity desired to move the diaphragm to the target measuring position, the actual volume defined by the one or more connection elements used to couple the air pump apparatus to the transducer side cavity, and a compliance of the one or more tubes.

10. The system of claim 1, wherein the pressure measurement apparatus is provided as part of an extracorporeal blood set comprising a plurality of pressure measurement apparatus mountable on a system housing containing at least the controller and at least one pressure transducer corresponding to each of the plurality of pressure measurement apparatus, and further wherein the system comprises a plurality of valves, wherein the controller is configured to operate a different valve for each of the plurality of pressure measurement apparatus mounted on the system housing to allow the diaphragm of each of the pressure measurement apparatus to be separately repositioned during different time periods using the air pump apparatus.

11. The system of claim 10, wherein the controller is configured to use air pressure measurements from the pressure transducer corresponding to a pressure measurement apparatus for therapy pressure monitoring prior to repositioning the diaphragm of the pressure measurement apparatus and is configured to temporarily discontinue the use of the air pressure measurements from the corresponding pressure transducer for therapy pressure monitoring when the diaphragm is being repositioned.

12. A pressure measurement method for an extracorporeal blood treatment system, the method comprising:

providing a pressure measurement apparatus comprising:
at least a pod body portion and a base body portion; and
a diaphragm separating a fluid side cavity defined at least in part by the pod body portion from a transducer side cavity defined at least in part by the base body portion, wherein the fluid side cavity is in fluid communication with an inlet and an outlet, and further wherein the diaphragm is displaceable from a target measuring position into the fluid side cavity towards the pod body portion and is displaceable from the target measuring position into the transducer side cavity towards the base body portion;

providing an air pump apparatus coupled to the transducer side cavity via one or more connection elements to add air to or remove air from the transducer side cavity;

controlling the air pump apparatus to bottom out the diaphragm on the base body portion by removing air from the transducer side cavity or to top out the diaphragm on the pod body portion by adding air to the transducer side cavity;

monitoring the air pressure in the transducer side cavity; and controlling the air pump apparatus to add air to the transducer side cavity after the diaphragm is bottomed out to move the diaphragm toward a target measuring position based on a calculated target air volume or to remove air from the transducer side cavity after the diaphragm is topped out to move the diaphragm toward a target measuring position based on the calculated target air volume, wherein the calculated target air volume is representative of the air volume necessary to move the diaphragm to the target measuring position based at least on the monitored air pressure, and further wherein, as air is added to or removed from the transducer side cavity, the target air volume is iteratively calculated until it is determined that the diaphragm is repositioned in the target measuring position based on a comparison of the calculated target air volume and a total amount of air added to or removed by the air pump apparatus.

13. The method of claim 12, wherein determining that the diaphragm is repositioned in the target measuring position comprises determining that the diaphragm is in the target measuring position when the amount of air added to or removed from the transducer side cavity meets the calculated target air volume.

14. The method of claim 12, wherein the calculation of target air volume is adjusted for atmospheric conditions.

15. The method of claim 14, wherein the calculation of target air volume is adjusted using a user input value representative of atmospheric pressure at a particular location.

16. The method of claim 14, wherein the calculation of target air volume is adjusted using a value representative of atmospheric pressure measured by an atmospheric pressure sensor of the system.

17. The method of claim 12, wherein the amount of air added to or removed from the transducer side cavity is determined by monitoring rotation of the air pump apparatus which delivers a known amount of air per rotation.

18. The method of claim 12, wherein calculating the target air volume necessary to move the diaphragm to the target measuring position comprises calculating the target air volume based at least on the monitored air pressure, an actual volume defined by the transducer side cavity desired to move the diaphragm to the target measuring position, and an actual volume defined by the one or more connection elements used to couple the air pump apparatus to the transducer side cavity of the pressure measurement apparatus.

19. The method of claim 18, wherein the one or more connection elements used to couple the air pump apparatus to the transducer side cavity comprise one or more tubes, and further wherein calculating the target air volume necessary to move the diaphragm to the target measuring position comprises calculating the target air volume based at least on the monitored air pressure, the actual volume defined by the transducer side cavity desired to move the diaphragm to the target measuring position, the actual volume defined by the one or more connection elements used to couple the air pump apparatus to the transducer side cavity, and a compliance of the one or more tubes.

20. The method of claim 12, wherein the pressure measurement apparatus is provided as part of an extracorporeal blood set comprising a plurality of pressure measurement apparatus mountable on a system housing containing at least the controller and at least one pressure transducer corresponding to each of the plurality of pressure measurement apparatus for monitoring pressure within the transducer side cavity of the corresponding pressure measurement apparatus, and further wherein the method comprises:
   using air pressure measurements from a pressure transducer corresponding to a pressure measurement apparatus for therapy pressure monitoring prior to repositioning the diaphragm; and
   temporarily discontinuing the use of the air pressure measurements from the pressure transducer corresponding to the pressure measurement apparatus for therapy pressure monitoring when the diaphragm is being repositioned.

* * * * *